(12) United States Patent
Sadowski et al.

(10) Patent No.: US 10,774,169 B2
(45) Date of Patent: Sep. 15, 2020

(54) BRUSH AMPHIPHILIC BLOCK COPOLYMERS, AND SELF-ASSEMBLED NANOPARTICLES THEREFROM

(71) Applicant: McMaster University, Hamilton (CA)

(72) Inventors: Lukas Sadowski, Toronto (CA); Todd Hoare, Ancaster (CA); Haiming (Daniel) Luo, Markham (CA); Maryam Badv, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 0 days.

(21) Appl. No.: 15/646,630

(22) Filed: Jul. 11, 2017

(65) Prior Publication Data

US 2018/0009924 A1    Jan. 11, 2018

Related U.S. Application Data

(60) Provisional application No. 62/360,615, filed on Jul. 11, 2016.

(51) Int. Cl.
| | |
|---|---|
| *C08F 293/00* | (2006.01) |
| *A61K 31/337* | (2006.01) |
| *A61K 31/704* | (2006.01) |
| *A61K 9/51* | (2006.01) |

(52) U.S. Cl.
CPC .......... *C08F 293/00* (2013.01); *A61K 9/5138* (2013.01); *A61K 31/337* (2013.01); *A61K 31/704* (2013.01); *C08F 293/005* (2013.01); *C08F 2438/01* (2013.01)

(58) Field of Classification Search
None
See application file for complete search history.

(56) References Cited

PUBLICATIONS

Xu et al., Colloids and Surfaces B: Biointerfaces 48 (2006), pp. 50-57.*
Jain, R. A., The manufacturing techniques of various drug loaded biodegradable poly(lactide-co-glycolide) (PLGA) devices. Biomaterials 2000, 21 (23), 2475-2490.
Danhier, F.; Ansorena, E.; Silva, J. M.; Coco, R.; Le Breton, A.; Preat, V., PPGA-based nanoparticles: An overview of biomedical applications. Journal of Controlled Release 2012, 161 (2), 505-522.
Zizelmann, C.; Schoen, R.; Metzger, M. C.; Schmelzeisen, R.; Schramm, A.; Dott, B.; Bormann, K. H.; Gellrich, N. C., Bone formation after sinus augmentation with engineered bone. Clin Oral Implan Res 2007, 18 (1), 69-73.
Azimi, B.; Nourpanah, P.; Rabiee, M.; Arbab, S., Poly (lactide-co-glycolide) Fiber: An Overview. J Eng Fiber Fabr 2014, 9 (1), 47-66.
Hickey, T.; Kreutzer, D.; Burgess, D. J.; Moussy, F., Dexamethasone/PLGA microspheres for continuous delivery of an anti-inflammatory drug for implantable medical devices. Biomaterials 2002, 23 (7), 1649-56.
Tamai, H.; Igaki, K.; Kyo, E.; Kosuga, K.; Kawashima, A.; Matsui, S.; Komori, H.; Tsuji, T.; Motohara, S.; Uehata, H., Initial and 6-month results of biodegradable poly-l-lactic acid coronary stents in humans. Circulation 2000, 102 (4), 399-404.
Wang, X. T.; Venkatraman, S. S.; Boey, F. Y. C.; Loo, J. S. C.; Tan, L. P., Controlled release of sirolimus from a multilayered PLGA stent matrix. Biomaterials 2006, 27 (32), 5588-5595.
Smeets, N. M. B.; Patenaude, M.; Kinio, D.; Yavitt, F. M.; Bakaic, E.; Yang, F. C.; Rheinstadter, M.; Hoare, T., Injectable hydrogels with in situ-forming hydrophobic domains: oligo(D,L-lactide) modified poly(oligoethylene glycol methacrylate) hydrogels. Polymer Chemistry 2014, 5 (23), 6811-6823.
Makadia, H. K.; Siegel, S. J., Poly Lactic-co-Glycolic Acid (PLGA) as Biodegradable Controlled Drug Delivery Carrier. Polymers (Basel) 2011, 3 (3), 1377-1397.
Xiao, R. Z.; Zeng, Z. W.; Zhou, G. L.; Wang, J. J.; Li, F. Z.; Wang, A. M., Recent advances in PEG-PLA block copolymer nanoparticles. International Journal of Nanomedicine, May 2010, 1057-1065.
Gref, R.; Luck, M.; Quellec, P.; Marchand, M.; Dellacherie, E.; Harnisch, S.; Blunk, T.; Muller, R. H., 'Stealth' corona-core nanoparticles surface modified by polyethylene glycol (PEG): influences of the corona (PEG chain length and surface density) and of the core composition on phagocytic uptake and plasma protein adsorption. Colloid Surface B 2000, 18 (3-4), 301-313.
Knop, K.; Hoogenboom, R.; Fischer, D.; Schubert, U. S., Poly(ethylene glycol) in drug delivery: pros and cons as well as potential alternatives. Angew Chem Int Ed Engl 2010, 49 (36), 6288-308.
Vonarbourg, A.; Passirani, C.; Saulnier, P.; Benoit, J. P., Parameters influencing the stealthiness of colloidal drug delivery systems. Biomaterials 2006, 27 (24), 4356-73.
Dai, Q.; Walkey, C.; Chan, W. C., Polyethylene glycol backfilling mitigates the negative impact of the protein corona on nanoparticle cell targeting. Angew Chem Int Ed Engl 2014, 53 (20), 5093-6.
Gillies, E. R.; Dy, E.; Frechet, J. M.; Szoka, F. C., Biological evaluation of polyester dendrimer: poly(ethylene oxide) "bow-tie" hybrids with tunable molecular weight and architecture. Mol Pharm 2005, 2 (2), 129-38.
Cheng, J.; Teply, B. A.; Sherifi, I.; Sung, J.; Luther, G.; Gu, F. X.; Levy-Nissenbaum, E.; Radovic-Moreno, A. F.; Langer, R.; Farokhzad, O. C., Formulation of functionalized PLGA-PEG nanoparticles for in vivo targeted drug delivery. Biomaterials 2007, 28 (5), 869-876.
Piazza, J.; Hoare, T.; Molinaro, L.; Terpstra, K.; Bhandari, J.; Selvaganapathy, P. R.; Gupta, B.; Mishra, R. K., Haloperidol-loaded intranasally administered lectin functionalized poly(ethylene glycol)-block-poly(D,L)-lactic-co-glycolic acid (PEG-PLGA) nanoparticles for the treatment of schizophrenia. Eur J Pharm Biopharm 2014, 87 (1), 30-9.
Wang, S.; Dormidontova, E. E., Nanoparticle design optimization for enhanced targeting: Monte Carlo simulations. Biomacromolecules, 2010, 11 (7), 1785-95.

(Continued)

*Primary Examiner* — Samantha L Shterengarts
(74) *Attorney, Agent, or Firm* — Bereskin & Parr LLP; Michael Fenwick

(57) ABSTRACT

The present application relates to brush amphiphilic block copolymers comprising at least one block which is hydrophilic and at least another block which is hydrophobic. The block copolymers can be used to prepare nanoparticles for biomedical applications including delivery of pharmaceuticals and other bioactive agents

18 Claims, 15 Drawing Sheets

(56) References Cited

PUBLICATIONS

Martinez-Veracoechea, F. J.; Frenkel, D., Designing super selectivity in multivalent nano-particle binding. Proc Natl Acad Sci U S A 2011, 108 (27), 10963-8.

Joralemon, M. J.; O'Reilly, R. K.; Hawker, C. J.; Wooley, K. L., Shell click-crosslinked (SCC) nanoparticles: a new methodology for synthesis and orthogonal functionalization. J Am Chem Soc 2005, 127 (48), 16892-9.

O'Reilly, R. K.; Hawker, C. J.; Wooley, K. L., Cross-linked block copolymer micelles: functional nanostructures of great potential and versatility. Chem Soc Rev 2006, 35 (11), 1068-83.

Oh, J. K., Polylactide (PLA)-based amphiphilic block copolymers: synthesis, self-assembly, and biomedical applications. Soft Matter, 2011, 7 (11), 5096-5108.

Rowe, M. A.; Hammer, B. A. G.; Boyes, S. G., Synthesis of surface-initiated stimuli-responsive diblock copolymer brushes utilizing a combination of ATRP and RAFT polymerization techniques. Macromolecules 2008, 41 (12), 4147-4157.

Lego, B.; Francois, M.; Skene, W. G.; Giasson, S., Polymer Brush Covalently Attached to OH-Functionalized Mica Surface via Surface-Initiated ATRP: Control of Grafting Density and Polymer Chain Length. Langmuir 2009, 25 (9), 5313-5321.

Akimoto, J.; Nakayama, M.; Sakai, K.; Okano, T., Temperature-Induced Intracellular Uptake of Thermoresponsive Polymeric Micelles. Biomacromolecules 2009, 10 (6), 1331-1336.

Cao, Z. Q.; Yu, Q. M.; Xue, H.; Cheng, G.; Jiang, S. Y., Nanoparticles for Drug Delivery Prepared from Amphiphilic PLGA Zwitterionic Block Copolymers with Sharp Contrast in Polarity between Two Blocks. Angew Chem Int Edit 2010, 49 (22), 3771-3776.

Nam, K. W.; Watanabe, J.; Ishihara, K., Characterization of the spontaneously forming hydrogels composed of water-soluble phospholipid polymers. Biomacromolecules 2002, 3 (1), 100-105.

Watanabe, J.; Eriguchi, T.; Ishihara, K., Cell adhesion and morphology in porous scaffold based on enantiomeric poly (lactic acid) graft-type phospholipid polymers. Biomacromolecules 2002, 3 (6), 1375-1383.

Saeed, A. O.; Dey, S.; Howdle, S. M.; Thurecht, K. J.; Alexander, C., One-pot controlled synthesis of biodegradable and biocompatible co-polymer micelles. J Mater Chem 2009, 19 (26), 4529-4535.

Ishimoto, K.; Arimoto, M.; Okuda, T.; Yamaguchi, S.; Aso, Y.; Ohara, H.; Kobayashi, S.; Ishii, M.; Morita, K.; Yamashita, H.; Yabuuchi, N., Biobased Polymers: Synthesis of Graft Copolymers and Comb Polymers Using Lactic Acid Macromonomer and Properties of the Product Polymers. Biomacromolecules 2012, 13 (11), 3757-3768.

Zhang, K. R.; Tang, X.; Zhang, J.; Lu, W.; Lin, X.; Zhang, Y.; Tian, B.; Yang, H.; He, H. B., PEG-PLGA copolymers: Their structure and structure-influenced drug delivery applications. J Control Release 2014, 183, 77-86.

Shipp, D. A.; Wang, J. L.; Matyjaszewski, K., Synthesis of acrylate and methacrylate block copolymers using atom transfer radical polymerization. Macromolecules 1998, 31 (23), 8005-8008.

Han, J.; Zhu, Z. X.; Qian, H. T.; Wohl, A. R.; Beaman, C. J.; Hoye, T. R.; Macosko, C. W., A simple confined impingement jets mixer for flash nanoprecipitation. J Pharm Sci-Us 2012, 101 (10), 4018-4023.

Johnson, B. K.; Prud'homme, R. K., Flash NanoPrecipitation of organic actives and block copolymers using a confined impinging jets mixer. Aust J Chem 2003, 56 (10), 1021-1024.

Johnson, B. K.; Prud'homme, R. K., Chemical processing and micromixing in confined impinging jets. Aiche J 2003, 49 (9), 2264-2282.

Kim, Y.; Chung, B. L.; Ma, M. M.; Mulder, W. J. M.; Fayad, Z. A.; Farokhzad, O. C.; Langer, R., Mass Production and Size Control of Lipid-Polymer Hybrid Nanoparticles through Controlled Microvortices. Nano Lett 2013, 13 (10), 4997-4997.

Iyer, A. K.; Khaled, G.; Fang, J.; Maeda, H., Exploiting the enhanced permeability and retention effect for tumor targeting. Drug Discov Today 2006, 11 (17-18), 812-818.

Pustulka, K. M.; Wohl, A. R.; Lee, H. S.; Michel, A. R.; Han, J.; Hoye, T. R.; McCormick, A. V.; Panyam, J.; Macosko, C. W., Flash Nanoprecipitation: Particle Structure and Stability. Mol Pharmaceut 2013, 10 (11), 4367-4377.

Venkatraman, S. S.; Jie, P.; Min, F.; Freddy, B. Y. C.; Leong-Huat, G., Micelle-like nanoparticles of PLA-PEG-PLA triblock copolymer as chemotherapeutic carrier. Int J Pharm 2005, 298 (1), 219-232.

Bilati, U.; Allemann, E.; Doelker, E., Development of a nanoprecipitation method intended for the entrapment of hydrophilic drugs into nanoparticles. Eur J Pharm Sci 2005, 24 (1), 67-75.

Lutz, J. F.; Hoth, A., Preparation of ideal PEG analogues with a tunable thermosensitivity by controlled radical copolymerization of 2-(2-methoxyethoxy)ethyl methacrylate and oligo(ethylene glycol) methacrylate. Macromolecules 2006, 39 (2), 893-896.

Voytik-Harbin, S. L.; Brightman, A. O.; Waisner, B.; Lamar, C. H.; Badylak, S. F., Application and evaluation of the alamarBlue assay for cell growth and survival of fibroblasts. In Vitro Cell Dev-An 1998, 34 (3), 239-246.

\* cited by examiner

BRUSH AMPHIPHILIC BLOCK COPOLYMERS, AND SELF-ASSEMBLED NANOPARTICLES THEREFROM

RELATED APPLICATIONS

The present application claims the benefit of priority from U.S. provisional patent application No. 62/360,615 filed on Jul. 11, 2016, the contents of which are incorporated herein by reference in their entirety.

FIELD

The present application relates to brush amphiphilic block copolymers comprising at least one block which is hydrophilic and at least another block which is hydrophobic. The block copolymers can be used to prepare nanoparticles for biomedical applications including delivery of pharmaceuticals and other bioactive agents.

BACKGROUND

Poly(lactic acid) (PLA) and poly(lactic-co-glycolic acid) (PLGA) have been widely applied as polymeric scaffolds in a wide range of biomedical applications, including tissue engineering, drug delivery, bioresorbable sutures and as implantable devices in dentistry.[1] PL(G)A-based polymers offer particular benefits in terms of engineering a variety of controlled release vehicles, with drug-loaded sutures,[2] microspheres,[3] nanoparticles,[1b] stents[4] and as blends within hydrogel networks[5] all having been reported (some of which are used clinically). The widespread use of PL(G)A stems from the non-toxicity of the polymer, the safety and potential for clearance of its degradation products, its processibility, and its largely favorable mechanical properties for implantable devices.[6] Moreover, tunable chemical stability of the polymer can be achieved by controlling the ratio of lactic acid and glycolic acid repeat units in the backbone, enabling the preparation of materials with tailored degradation profiles and thus drug release profiles.[1b,6]

Owing to its relatively hydrophobic nature, PL(G)A has also been used as a degradable and cytocompatible hydrophobic block for the formation of amphiphilic block copolymers that can subsequently be self-assembled into nanoparticle (NP) formulations for drug delivery. Block copolymers of PL(G)A and poly(ethylene glycol) (PEG), both blocks of which have regulatory approval in a range of biomedical applications, have been particularly investigated as a promising precursor for NP formulations,[7] exploiting the hydrophobicity of PL(G)A to drive assembly and effectively load (and thus deliver) drugs with poor water solubility, the tunable degradability of PL(G)A to control release of that drug (at least within the window of potential degradation times and drug-polymer affinities facilitated by the PL(G)A chemistry), and the protein-repellency of PEG to avoid non-specific uptake and promote long circulation times in vivo.[8] End group functionalization of the PEG chains has also been used for the attachment of ligands to enable targeting of disease[9]. Using this strategy, it is possible to achieve higher uptake within the site of disease and/or target tissues that might otherwise be inaccessible.

However, while PL(G)A-PEG has been used successfully in drug delivery applications, the chemical nature of the polymer inherently limits its potential for functionalization. Given that both polymer blocks are made via ring-opening polymerization, reactive functional groups available for any post-functionalization strategy are only present at chain ends, limiting (for example) the ligand grafting density (often key to optimize to promote cooperative cell responses to those ligands[10]), the potential to engineer the affinity of the drug for the scaffold, and/or the potential to post-stabilize a self-assembled nanoparticle with covalent cross-links[11]. More recent development of functional ring-opening monomers has partially addressed this limitation, but such monomers still suffer from low conversions and the need to use protecting group chemistry to preserve the desired functional group during the polymerization process. Similarly, based on these same challenges inherent in including other functional monomers in ring-opening polymerizations, degradation of PL(G)A can only be tuned within a defined time window based on the L:G ratio and the interfacial properties (including potential smart properties) of the PEG phase are limited.

SUMMARY

The present disclosure relates to brush amphiphilic block copolymers comprising at least one block which is hydrophilic and at least another block which is hydrophobic. In another embodiment, the at least one hydrophilic block comprises a monomer containing a side chain with at least two hydrophilic repeat units and the at least one hydrophobic block comprises a monomer containing a side chain with at least two hydrophobic repeat units.

In one embodiment, the block copolymers form nanoparticles that are stable for tunable periods of time, degrade into generally recognized as safe components, and have low cell cytotoxicity.

In one embodiment, the brush amphiphilic block copolymer comprises a) at least one hydrophilic block comprising monomeric units of:

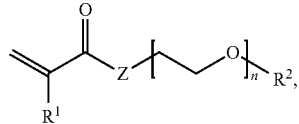

wherein
$R^1$ is H or $(C_1\text{-}C_6)$-alkyl, optionally substituted with —COOR, —COSR or —CON(R)$_2$, wherein R is independently or simultaneously H or $(C_1\text{-}C_6)$-alkyl;
$R^2$ is H, $(C_1\text{-}C_{20})$-alkyl, $(C_2\text{-}C_{24})$-alkenyl, $(C_2\text{-}C_{24})$-alkynyl, $(C_6\text{-}C_{14})$-aryl, $(C_5\text{-}C_{14})$-heteroaryl, or $(C_1\text{-}C_{10})$-alkylene-$(C_6\text{-}C_{14})$-aryl, wherein the latter 6 groups:
(i) are optionally substituted with halo, OH, COOH, or $(C_1\text{-}C_6)$-alkyl;
(ii) 1-3 carbon atoms are optionally replaced with O, NR', or C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or heterocycle (such as triazole);
Z is O, NR' or S;
R' is H or $(C_1\text{-}C_6)$-alkyl; and
n is at least 2;
b) at least one hydrophobic block comprising monomeric units of

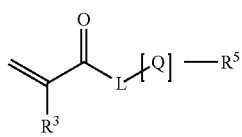

wherein
R³ is H or (C₁-C₆)-alkyl, optionally substituted with —COOR, —COSR or —CON(R)₂, wherein R is H or (C₁-C₆)-alkyl;
L is a linker;
Q is a hydrophobic polymer or copolymer; and
R⁵ is H, (C₁-C₂₀)-alkyl, (C₂-C₂₄)-alkenyl, (C₂-C₂₄)-alkynyl, (C₆-C₁₄)-aryl, (C₅-C₁₄)-heteroaryl, or (C₁-C₁₀)-alkylene-(C₆-C₁₄)-aryl, wherein the latter 6 groups:
(i) are optionally substituted with halo, OH, COOH, or (C₁-C₆)-alkyl;
(ii) 1-3 carbon atoms are optionally replaced with O, NR', or C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or heterocycle (such as triazole).

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE FIGURES

The embodiments of the application will now be described in greater detail with reference to the attached drawings in which.

DETAILED DESCRIPTION

I. Definitions

Figure 1:
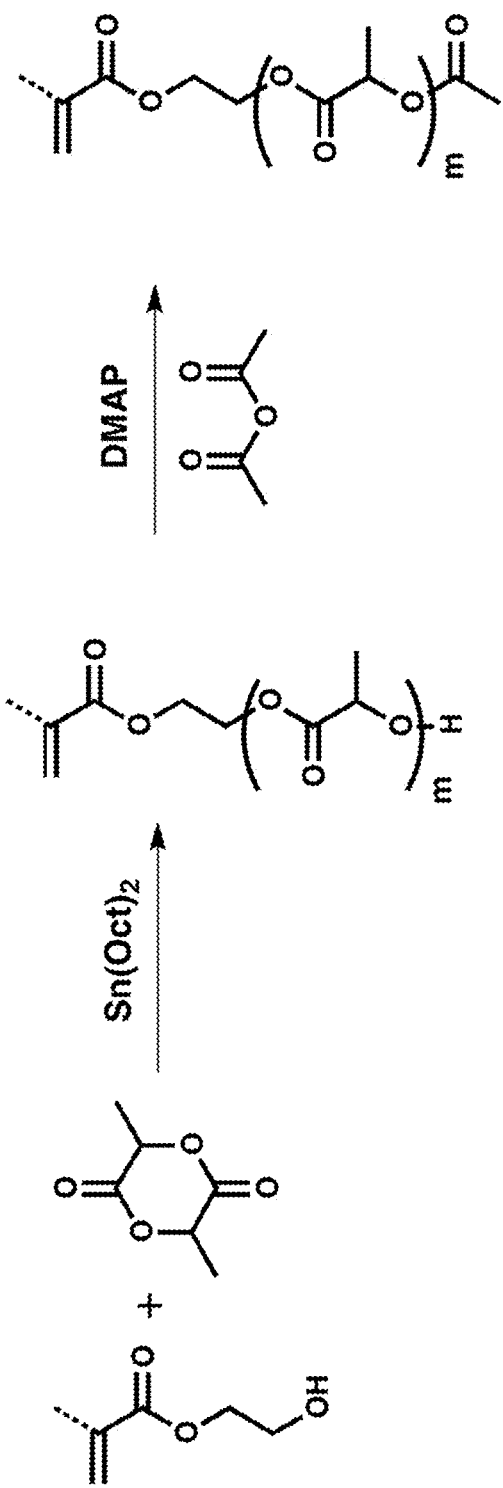
FIG. 1 shows the synthetic scheme of hydrophobic block (OLA(M)A) monomers and subsequent functionalization (acetylation) of the terminal alcohol.

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical terms and abbreviations used by those skilled in the art. Nevertheless, definitions of selected terms are provided for clarity and consistency.

As used in this application, the singular forms "a", "an" and "the" include plural references unless the content clearly dictates otherwise. For example, an embodiment including "the polymer" should be understood to present certain aspects with one compound or two or more additional compounds.

In embodiments comprising an "additional" or "second" component, such as an additional or second polymer, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "alkyl" as used herein, whether it is used alone or as part of another group, means straight or branched chain, saturated alkyl groups, and includes for example, methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, n-heptyl and the like. The term $C_{1-6}$ alkyl, for example, means an alkyl group having 1, 2, 3, 4, 5, or 6 carbon atoms.

The term "aryl" as used herein means a monocyclic, bicyclic or tricyclic aromatic ring system containing, depending on the number of atoms in the rings, for example from 6 to 14 carbon atoms, and at least 1 aromatic ring and includes phenyl, naphthyl, anthracenyl, 1,2-dihydronaphthyl, 1,2,3,4-tetrahydronaphthyl, fluorenyl, indanyl, indenyl and the like.

The term "heteroaryl" or "heteroaromatic" as used herein means a monocyclic, bicyclic or tricyclic ring system containing one or two aromatic rings, and from 5 to 14 atoms, optionally 5 or 6 atoms, of which, unless otherwise specified, one, two, three, four or five are a heteromoiety independently selected from N, NH, $NC_{1-6}$ alkyl, O and S and includes thienyl, furyl, pyrrolyl, pyrididyl, indolyl, quinolyl, isoquinolyl, tetrahydroquinolyl, benzofuryl, benzothienyl and the like.

The term "alkenyl" as used herein means straight or branched chain, unsaturated alkyl groups and contains one to three double bonds, and includes vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

The term "alkynyl" as used herein means straight and/or branched chain, unsaturated alkyl groups containing one or more, suitably one to three, triple bonds, and includes ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl4-methylpent-2-ynyl, 1-hexynyl and the like.

The suffix "ene" added on to any of the above groups means that the group is divalent, i.e. inserted between two other groups.

The term "halo" or "halogen" as used herein means halogen and includes chloro, fluoro, bromo and iodo.

The term "linker", as used herein, refers to a chemical moiety linking at least two other entities together, and involves covalent bonding The term "hydrophobic" as used herein refers to a chemical moiety or moieties within the hydrophobic monomer which lack an affinity for water.

The term "hydrophilic" as used herein refers to a chemical moiety or moieties within the hydrophilic monomer which have an affinity for water.

The term "amphiphilic" as used herein describes a structure having discrete hydrophobic and hydrophilic regions.

The term "hydrophobic polymer or copolymer" in the hydrophobic block as used herein refers to a polymer or copolymer which lacks an affinity to water and is prepared substantially from hydrophobic monomers.

The term "copolymer" as used herein refers to a polymer comprising two or more chemically-distinct monomeric subunits. These monomeric subunits are covalently attached to one another in a single polymer chain.

The term "block copolymer" as used herein refers to a copolymer comprising two or more different types of monomeric subunits (monomers), wherein the monomeric subunits are grouped into blocks containing only one type of monomeric subunit or two or more comonomers that have like properties (i.e. water soluble or water insoluble). For example, the monomeric subunits can be grouped into separate and distinct combinations in different parts of the overall polymer chain, and can contain 2 or more monomers in each block. These blocks are covalently attached to other blocks containing different subunits in the same polymer chain.

The term "brush copolymer" refers to a copolymer where at least one of the monomeric units (monomers) is derived from a macromonomer which contains a polymeric (side) chain (for example, containing at least 2 repeat units) and which also has a polymerizable group.

The term "functional group" refers to reactive groups that are capable of reacting with other molecules to form new moieties, groups or conjugates.

II. Brush Amphiphilic Block Copolymers

The present disclosure relates to brush amphiphilic block copolymers comprising at least one block which is hydrophilic and at least another block which is hydrophobic. In one embodiment, the hydrophilic block is comprised of primarily hydrophilic monomers and the hydrophobic block is comprised of primarily hydrophobic monomers, wherein the hydrophilic and hydrophobic monomers comprise a polymerizable moiety, which is polymerizable through controlled radical polymerization. In another embodiment, the at least one hydrophilic block comprises at least one monomer containing a side chain with at least two hydrophilic repeat units and the at least one hydrophobic block comprises at least one monomer containing a side chain with at least two hydrophobic repeat units.

In one embodiment, the hydrophilic block monomer contains a side chain with at least two hydrophilic repeat units, wherein the hydrophilic repeat units comprise a polyethylene glycol moiety and further contains a polymerizable group which is ethylenically unsaturated. In one embodiment, the hydrophilic block monomer is poly(oligoethylene glycol methacrylate), poly(oligoethylene glycol acrylate), or a combination thereof. In one embodiment, the hydrophilic block monomer comprises a polyethylene glycol moiety having at least two repeat units, for example, between 2 and 50 repeats units, or about 2 and 30 repeat units.

In another embodiment, the hydrophobic block monomer contains one or more side chains with at least two hydrophobic repeat units, wherein the hydrophobic repeat units comprise one or more biodegradable repeat units, for example, a water-insoluble (hydrophobic) polyester or polyamide, and further contains the a polymerizable group which is ethylenically unsaturated. In one embodiment, the polyester is polylactic acid, polyglycolic acid, polycaprolactone, or copolymers thereof. In another embodiment. In one embodiment, the hydrophobic block monomer comprises poly(oligolactic acid methacrylate), poly(oligoglycolic acid methacrylate), poly(oligolactic acid acrylate), poly(oligoglycolic acid acrylate), a combinations thereof. In one embodiment, the hydrophoic block monomer comprises a hydrophobic moiety unit having at least two repeat units, for example, between 2 and 50 repeats units, or about 2 and 30 repeat units.

In another embodiment, the hydrophobic and hydrophilic monomers are side-chain terminated with a functional end group including (but not limited to) a hydrophobic group, a hydrophilic group, a fluorescent probe, a metal chelating moiety, a radionuclide, a pH-ionizable group, a cell binding or targeting group, or another functional entity.

In another embodiment, the block copolymer further comprises one or more additional monomers having a polymerizable moiety, such as an ethylenically unsaturated moiety, and a functional group, for example, a carboxy group, ester, amino group, thiol group, hydroxyl group, or halide, etc. In one embodiment, the polymerizable moiety is an acrylate or methacrylate moiety.

In one embodiment, each block copolymer is comprised of at least about 50%, or least about 60%, or least about 70%, of hydrophilic and hydrophobic monomers. In another embodiment, the brush amphiphilic block copolymers of the present disclosure contain hydrophilic and hydrophobic monomers in a ratio between about 5:95 to about 95:5 (w/w) of hydrophilic monomers:hydrophobic monomers. In another embodiment, each polymer block of the block copolymers of the present disclosure has a molecular weight of between about 500 to about 100,000 Da.

In another embodiment, the brush amphiphilic block copolymer comprises a) at least one hydrophilic block comprising monomeric units of:

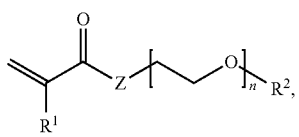

wherein $R^1$ is H or $(C_1-C_6)$-alkyl, optionally substituted with —COOR, —COSR or —CON(R)$_2$, wherein R is independently or simultaneously H or $(C_1-C_6)$-alkyl;

$R^2$ is H, $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
(i) are optionally substituted with halo, OH, or $(C_1-C_6)$-alkyl;
(ii) 1-3 carbon atoms are optionally replaced with O, NR', or C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or heterocycles (such as triazoles);

Z is O, NR' or S;
R' is H or $(C_1-C_6)$-alkyl; and
n is at least 2;

b) at least one hydrophobic block comprising monomeric units of

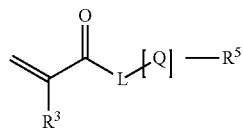

wherein $R^3$ is H or $(C_1-C_6)$-alkyl, optionally substituted with —COOR, —COSR or —CON(R)$_2$, wherein R is independently or simultaneously H or $(C_1-C_6)$-alkyl;

L is a linker;

Q is a hydrophobic polymer or copolymer; and $R^5$ is H, $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
(i) are optionally substituted with halo, OH, or $(C_1-C_6)$-alkyl;
(ii) 1-3 carbon atoms are optionally replaced with O, NR', or C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, sulfone, sulfonate, phosphoesters, phosphoramidates, phosphazenes, and/or heterocycles (such as triazoles).

In one embodiment, the hydrophobic polymer or copolymer is comprised of hydrophobic monomeric units. In another embodiment, the hydrophobic polymer or copolymer is a polyurethane, polythiourethane, polyether, polyamide, polyester, polyphosphazine, polyphosphamide, polyphosphodiester, polyurea, polythiourea, polyfumurate, or polyanhydride.

In another embodiment, the linker L is $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
(i) are optionally substituted with halo, OH, COOH, or $(C_1-C_6)$-alkyl;
(ii) 1-3 carbon atoms are optionally replaced with O, NR', or C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or heterocycle (such as triazole).

In another embodiment, the linker L is $(C_1-C_{20})$-alkyl, or $(C_1-C_{10})$-alkyl, which is optionally substituted with —COOH; optionally 1-3 atoms are replaced with O or C(=O), for example, an ester functionality [—C(=O)—O) or —O—C(=O)], and wherein the group optionally contains one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or a heterocycle.

In another embodiment of the disclosure, the at least one hydrophobic block comprises monomeric units of

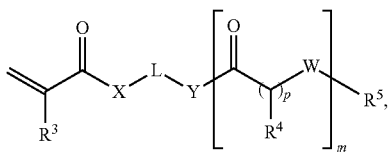

wherein
$R^3$ is H or $(C_1-C_6)$-alkyl, optionally substituted with —COOR, —COSR or —CON(R)$_2$, wherein R is independently or simultaneously H or $(C_1-C_6)$-alkyl;
each $R^4$ is independently or simultaneously H, OH, COOH, or aryl, wherein the latter two groups may optionally contain functional groups which are esters, acids, thioesters, amides, ureas, thioureas, carbonates, carbamates, thiocarbamates, ethers, thioethers, primary, secondary, tertiary and/or quaternary amines, sulfonamides, sulfones, sulfonates, phosphoesters, phosphoramidates, phosphazenes, and/or a heterocycle (such as a triazole);
$R^5$ is H, $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
  (i) are optionally substituted with halo, OH, or $(C_1-C_6)$-alkyl;
  (ii) 1-3 carbon atoms are optionally replaced with O, NR', or C(=O); and/or
  (iii) optionally contain one or more functional groups comprising esters, thioesters, amides, ureas, thioureas, carbonates, carbamates, thiocarbamates, ethers, thioethers, primary, secondary, tertiary and/or quaternary amines, sulfone, sulfonate, phosphoesters, phosphoramidates, phosphazenes, and/or triazoles;
L is a linker;
X and Y are independently or simultaneously O, NR' or S;
W is O, —C(=O)—O—, —C(=O)—NR'—, —C(=S)—NR'—, or NR';
R' is H or $(C_1-C_6)$-alkyl;
each p is independently or simultaneously 1, 2, 3, 4, 5, 6, 7, 8, 9 or 10; and m is at least 2.

In another embodiment, $R^1$ is H or $(C_1-C_3)$-alkyl, optionally substituted with —COOH. In another embodiment, $R^1$ is H or $CH_3$.

In another embodiment, $R^2$ is H, $(C_2-C_{10})$-alkenyl, $(C_2-C_{10})$-alkynyl, $(C_6-C_{10})$-aryl, $(C_5-C_{10})$-heteroaryl, or $(C_1-C_{10})$-alkylene-$(C_6-C_{10})$-aryl. In another embodiment, $R^2$ is H, $(C_1-C_6)$-alkyl, $(C_2-C_6)$-alkenyl, $(C_2-C_6)$-alkynyl, $(C_6)$-aryl, $(C_5-C_6)$-heteroaryl, or $(C_1-C_6)$-alkylene-$(C_6)$-aryl. In another embodiment, $R^2$ is H, $(C_1-C_6)$-alkyl, $(C_6)$-aryl, $(C_5-C_6)$-heteroaryl, or $(C_1-C_3)$-alkylene-$(C_6)$-aryl. In another embodiment, the latter groups of $R^2$ are (i) are optionally substituted with $(C_1-C_6)$-alkyl; (ii) 1-3 carbon atoms are optionally replaced with C(=O) (for example, —C(=O)—$CH_3$); and/or (iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or a heterocycle (such as a triazole).

In another embodiment, n is an integer between 2 and 50, or 2 and 30.

In another embodiment, $R^3$ is H or $(C_1-C_3)$-alkyl, optionally substituted with —COOH. In another embodiment, $R^3$ is H or $CH_3$.

In another embodiment, $R^5$ is H, $(C_2-C_{10})$-alkenyl, $(C_2-C_{10})$-alkynyl, $(C_6-C_{10})$-aryl, $(C_5-C_{10})$-heteroaryl, or $(C_1-C_{10})$-alkylene-$(C_6-C_{10})$-aryl. In another embodiment, $R^5$ is H, $(C_1-C_6)$-alkyl, $(C_2-C_6)$-alkenyl, $(C_2-C_6)$-alkynyl, $(C_6)$-aryl, $(C_5-C_6)$-heteroaryl, or $(C_1-C_6)$-alkylene-$(C_6)$-aryl. In another embodiment, $R^5$ is H, $(C_1-C_6)$-alkyl, $(C_6)$-aryl, $(C_5-C_6)$-heteroaryl, or $(C_1-C_3)$-alkylene-$(C_6)$-aryl. In another embodiment, the latter groups of $R^2$ are (i) are optionally substituted with $(C_1-C_6)$-alkyl; (ii) 1-3 carbon atoms are optionally replaced with C(=O) (for example, —C(=O)—$CH_3$); and/or (iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or a heterocycle (such as a triazole).

In another embodiment, each $R^4$ is independently or simultaneously H, $(C_1-C_6)$-alkyl, or aryl, wherein the latter two groups may optionally contain esters, acids, thioesters, amides, ureas, thioureas, carbonates, carbamates, thiocarbamates, ethers, thioethers, primary, secondary, tertiary and/or quaternary amines, disulfides, sulfonamides, sulfones, sulfonates, phosphoesters, phosphoramidates, phosphazenes, and/or a heterocycle (such as a triazole).

In another embodiment, X and Y are O. In one embodiment, W is O.

In another embodiment, the linker L is $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
  (i) are optionally substituted with halo, OH, COOH, or $(C_1-C_6)$-alkyl;
  (ii) 1-3 carbon atoms are optionally replaced with O, NR', or C(=O); and/or
  (iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or heterocycle (such as triazole).

In another embodiment, the linker L is $(C_1-C_{20})$-alkyl, or $(C_1-C_{10})$-alkyl, which is optionally substituted with —COOH; optionally 1-3 atoms are replaced with O or C(=O), for example, an ester functionality [—C(=O)—O) or —O—C(=O)], and wherein the group optionally contains one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, and/or a heterocycle.

In another embodiment, p is 1, 2, 3, 4, 5, 6, 7 or 8.

In one embodiment, the structure of the hydrophobic moiety of the hydrophobic monomer as shown below

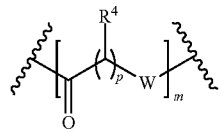

may be a copolymer, such that each $R^4$ and "p" may be the same or different depending on the identity of "m"; for example, if m is 2, then the first $R^4$ may be H, and the second $R^4$ may be methyl. In another embodiment, each "p" may be the same or different depending on the identity of "m"; for example, if m is 2, then the first "p" may be 1, and the second "p" may be 6.

In one embodiment, the hydrophobic monomer is comprised of monomers of lactic acid (L), glycolic acid (G) and/or caprolactone (C), and any of the copolymers therefrom. For example, if "m" is 5, the hydrophobic moiety of the hydrophobic monomer may be a copolymer of [L-L-C-L-L] or [L-L-G-G].

In one embodiment, one or both blocks impart stimulus-responsive properties to environmental variables including but not limited to pH, temperature, target chemicals, and ionic strength.

In a further embodiment of the disclosure, the hydrophilic block comprises monomeric units where n is 0 and $R^2$ is H, resulting in the following structure:

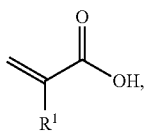

wherein
$R^1$ is H or $(C_1-C_6)$-alkyl.

In one embodiment, the block copolymers of the present disclosure allow for the introduction of additional capacity to tune the chemistry of each block by the introduction of functional groups, for example, through the addition of a third, fourth, or more additional monomers. In one embodiment, the addition of functional groups allows for the tuning of the block copolymers and to address the various demands and physiological barriers associated with diverse drug delivery applications and improve the clinical efficacy of nanoparticle-based drug formulations.

In another embodiment of the disclosure, the brush amphiphilic block copolymer further comprises one or more additional monomers which provide conjugation sites for small molecule or biomolecular ligands or affect the overall hydrophobicity or hydrophilicty of each block, or is conjugated to a targeting ligand. In one embodiment, the additional monomers have a polymerizable group which allows for incorporation into the block copolymer. In one embodiment, the polymerizable group is ethylenically unsaturated.

In one embodiment, the additional monomer(s) has the structure

wherein
$R^6$ is H or $(C_1-C_6)$-alkyl, optionally substituted with —COOR, —COSR or —CON(R)$_2$, wherein R is H or $(C_1-C_6)$-alkyl;

K is a functional group which is —R", —OR", —SR", —COOH, —COOR", CON(R")$_2$, —S—S—R", —R"OR", —R"SR", —R"COOR", R"CON(R")$_2$, R"—S—S—R", wherein R" is $(C_1-C_{10})$-alkyl, $(C_2-C_{10})$-alkenyl, $(C_2-C_{10})$-alkynyl, $(C_6-C_{10})$-aryl, $(C_5-C_{10})$-heteroaryl, or $(C_1-C_{10})$-alkylene-$(C_6-C_{10})$-aryl. In another embodiment, R" is $(C_1-C_6)$-alkyl, $(C_2-C_6)$-alkenyl, $(C_2-C_6)$-alkynyl, $(C_6)$-aryl, $(C_5-C_6)$-heteroaryl, or $(C_1-C_6)$-alkylene-$(C_6)$-aryl. In another embodiment, R" is $(C_1-C_3)$-alkyl, $(C_2-C_3)$-alkenyl, $(C_2-C_3)$-alkynyl, $(C_6)$-aryl, $(C_5-C_6)$-heteroaryl, or $(C_1-C_3)$-alkylene-$(C_6)$-aryl. In another embodiment, K is a $(C_1-C_{10})$-alkyl, which may optionally contain esters, acids, thioesters, amides, ureas, thioureas, carbonates, carbamates, thiocarbamates, ethers, thioethers, primary, secondary, tertiary and/or quaternary amines, disulfides, sulfonamides, sulfones, sulfonates, phosphoesters, phosphoramidates, phosphazenes, a hydrophilic or hydrophobic polymer as defined above, and/or a heterocycle (such as a triazole)

In one embodiment, $R^6$ is H or $(C_1-C_3)$-alkyl, or H or $CH_3$.

In another embodiment, the functional group is a carboxy group, ester, amino group, thiol group, hydroxyl group, or halide, and is optionally protected. In another embodiment, the additional monomer has the structure

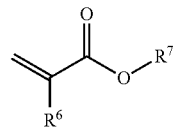

wherein
$R^6$ is H or $(C_1-C_6)$-alkyl, optionally substituted with —COOR, wherein R is H or $(C_1-C_6)$-alkyl; and
$R^7$ is a protecting group, such as $(C_1-C_6)$-alkyl.

In one embodiment, the additional monomer is t-butyl methacrylate, which can be deprotected after polymerization to form a carboxy group, which can then be further functionalized.

In one embodiment of the disclosure, the hydrophilic blocks and hydrophobic blocks are polymerized through the polymerizable moiety of the monomers through, for example, controlled radical polymerization. In one embodiment, the polymerizable moiety is an ethylenically unsaturated moiety, such as an acrylate moiety. For example, when the hydrophilic monomer has the structure (with all variables as described above)

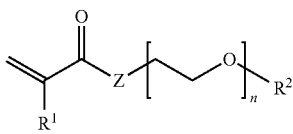

and the hydrophobic monomer has the structure

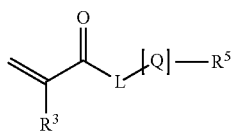

the resulting brush amphiphilic block copolymer has the structure (where each block can be alternately repeated)

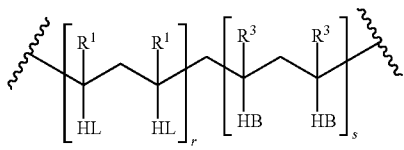

wherein HL is

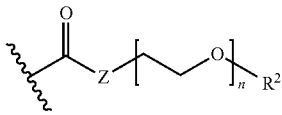

and HB is

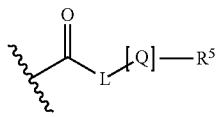

wherein
r is between 2 and 1000; and
s is between 2 and 1000.

In one embodiment, the block copolymers of the present disclosure are prepared through controlled radical polymerization through the polymerizable moieties, wherein, for example, a first block is prepared from the hydrophobic monomers using a radical initiator to form the hydrophobic block. Upon obtaining blocks of the desired size or molecular weight, the controlled radical polymerization is stopped. The polymerization is then continued using the hydrophobic blocks as initiators in the presence of the hydrophilic monomers to form the brush amphiphilic block copolymers. In one embodiment, the reaction may proceed using free radical polymerization. The addition of additional monomer(s) may be performed during the polymerization of either block, to form copolymers therefrom.

In a further embodiment, the brush amphiphilic block copolymers of the present disclosure form nanoparticles via self-assembly or directed assembly. In one embodiment, the nanoparticles are prepared by nanoprecipitation, flash nanoprecipitation, micro/nanofluidics, solvent exchange, emulsification/evaporation, or self-assembly, grinding. In one embodiment, the monomeric subunits of the block copolymer undergo phase segregated arrangement as a result of the affinity of the monomeric subunits to organize with similar monomeric subunits.

In another embodiment of the disclosure, the nanoparticles of the present disclosure encapsulate drugs or other bioactive agents, including hydrophobic and hydrophilic active agents.

The present disclosure also includes a composition comprising a nanoparticle formed from the block copolymers of the present disclosure which is loaded with one or more drugs or active agents. In one embodiment, the disclosure includes a pharmaceutical composition comprising a nanoparticle as described and a pharmaceutically acceptable excipient or diluent.

Accordingly, there are provided methods for using block copolymers for many biomedical applications, including drug delivery, imaging and theranostics.

Examples

The following non-limiting examples are illustrative of the present application:

Example 1: Block Polymer Synthesis

The OLAMA monomer was synthesized using a previously established protocol[17]. The initiator BnBiB was synthesized using a previously established protocol.[31] In an Schlenk flask equipped with a magnetic stir bar, 1 equivalent of BnBiB, 1.25 equivalents of bipyridine (BiPy) and OLAMA monomer (equivalents dependent on the molecular weight target, see Table 1) were dissolved in dimethyl sulfoxide (DMSO). The solution was subjected to 3 cycles of freeze-pump-thaw for degassing. During the second freeze cycle, 0.63 equivalents of CuBr were added before continuing. After degassing, the reaction was left stirring at 80° C. for 2 hours. Air was introduced to halt the continuation of the reaction. The solution was then filtered through basic alumina to remove the copper catalyst and solvent was evaporated under vacuum. The reaction was precipitated into cold ethyl ether to remove unreacted monomer, with the precipitate collected and dried.

To chain extend the POLAMA block with the POEGMA block, 1 equivalent of POLAMA polymer, 2.5 equivalents of BiPy, PMDETA or Me$_6$TREN, and OEGMA (MW 475 g/mol) monomer (equivalents vary depending on molecular weight target, see Table 2) were dissolved in a 5 mL solution of 50:50 v/v % EtOH and DMSO mixture in an Schlenk flask equipped with a magnetic stir bar. The solution was subjected to 3 cycles of freeze pump thaw. During the second freeze procedure, 1 equivalent of CuCl was added before continuing. After degassing, the reaction was left stirring at 60° C. for 6 hours. Air was introduced to halt the reaction, after which the solution was then filtered through basic alumina to remove the copper catalyst and solvent was evaporated under vacuum. The reaction was precipitated into cold ethyl ether twice to remove unreacted monomers. The precipitate was collected and dried.

Polymer Characterization:

NMR spectra was acquired on a Bruker 600 MHz spectrometer and calibrated to the residual solvent signal. GPC data was acquired on a Polymer Laboratories PL-50 GPC equipped with three Phenomenex Phenogel™ columns (300×4.6 mm, 5 μm; pore sizes: 100, 500, 10$^4$ Å) at room temperature; DMF with 50 mM LiBr was used as the eluent, and calibration was performed using linear PEG standards obtained from Polymer Laboratories. All samples were filtered using a 0.2 μm Teflon filter prior to analysis.

Figure 2:
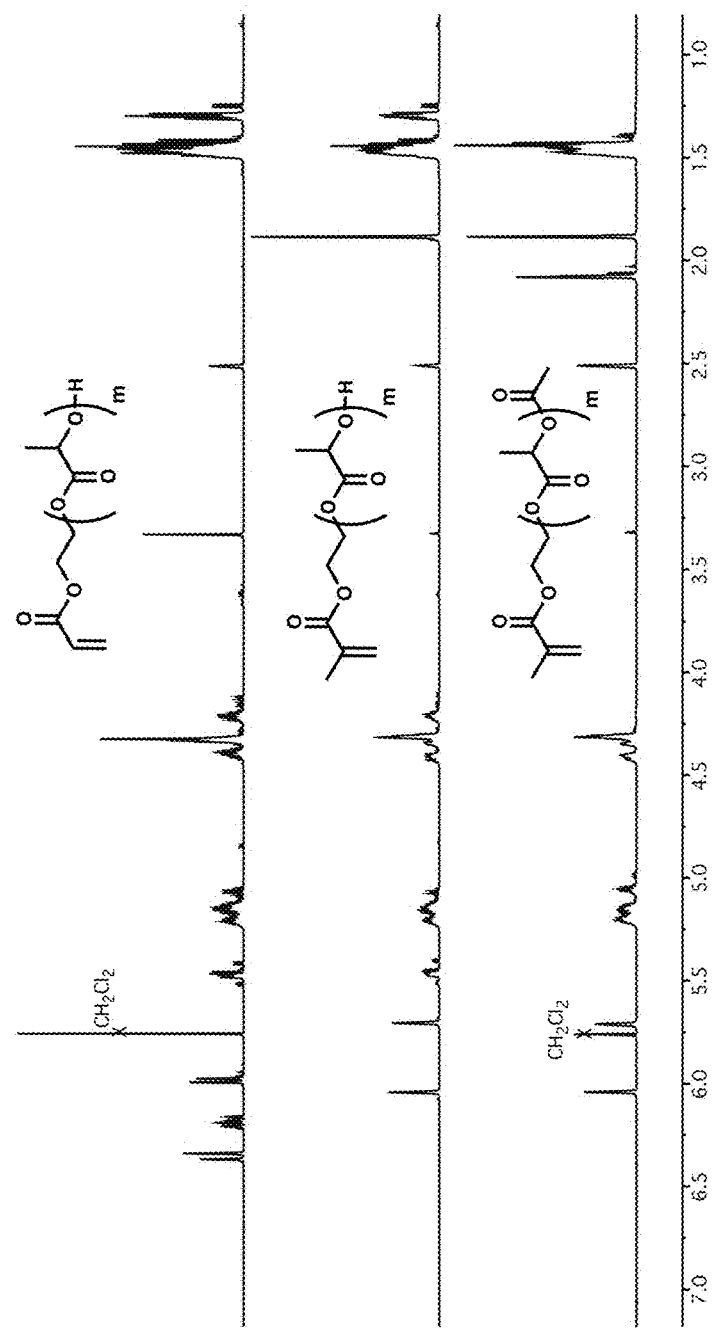
FIG. 2 shows the ¹H-NMR spectrum in DMSO-d6 of various hydrophobic block oligo(lactic acid) acrylate monomer (top), oligo(lactic acid) methacrylate monomer (middle) and acetylated oligo(lactic acid) methacrylate monomer (bottom).

Polymerization of the first block using the OLAMA macromonomer, prepared by the Sn(II) catalyzed ring opening polymerization of 2-hydroxyethyl methacrylate with lactide monomer[17] (lactic acid repeat units (m)=4 or 8), was conducted at 70° C. in DMSO to afford a series of polymers with number average molecular weights ($M_n$) ranging from 10-45 kDa, as measured using gel permeation chromatography relative to a linear PEG control (Table 1). All polymers exhibited a dispersity ($Đ$) below 1.27; while this number represents only a moderate degree of control for a conventional linear polymer, the brush nature of the POLAMA block (and polydispersity within the monomer) inherently leads to higher $Đ$ values such that the measured result represents relatively good polymerization control. The benzyl group on the initiator allowed for accurate quantification of conversion and molecular weight by $^1$H-NMR spectroscopy, which was in relatively good agreement with the results obtained by GPC (Table 1). The POLAMA polymers were subsequently used as macroinitiators for chain extension with the hydrophilic OEGMA monomer using a 1:1 MeOH/DMSO solvent mixture (Table 2). GPC gives direct evidence of the efficacy of the chain extension with POEGMA, with a clear shift toward higher molecular weights evident in the GPC molecular weight distributions (FIG. 2). It is important to note that halide exchange through the use of CuCl had to be employed in order to maintain control over polymerization of the POEGMA block.[19]

Figure 3:
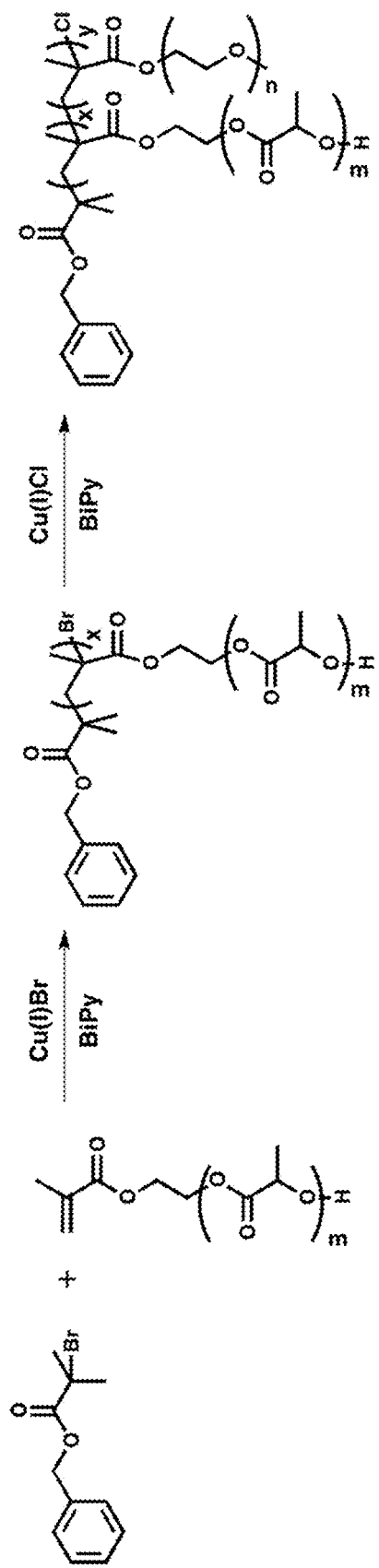
FIG. 3 shows the synthetic scheme of a block copolymer of the disclosure (POLAMA-b-POEGMA) prepared via ATRP in one embodiment of the disclosure.

Functional group incorporation was demonstrated by copolymerizing tert-butyl methacrylate (5% compared to the OLAMA monomer) within the POLAMA block (FIG. 3) The resulting polymer exhibited living character, as evidenced by the chain extension with OEGMA, resulting in an amphiphilic block copolymer. Removal of the tert-butyl group to unmask the carboxylic acid was accomplished under standard acidic conditions using trifluoroacetic acid, as evidenced by the disappearance of the tert-butyl protons at 1.37 ppm. All block copolymers exhibited a $Đ$ below 1.36, demonstrating control over polymerization of each block in the context of the dual brush morphology of the copolymer produced. Similar results were obtained via incorporation of amine functionality by way of a 'Boc-protected amine monomer followed by protecting group removal under acidic conditions. In principle, any functional group could be added using a similar protected (or if compatible with ATRP or another controlled radical polymerization technique unprotected) monomer.

Figure 13:
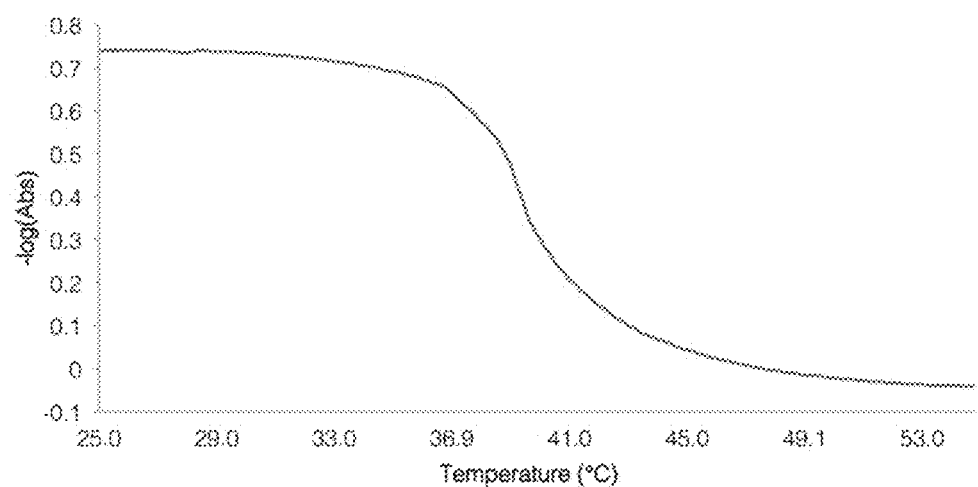
FIG. 13 shows the temperature dependent phase transition of nanoparticles composed of a block copolymer of the disclosure (POLAMA4-POEGMA) bearing diethylene glycol methacrylate and oligo(ethylene glycol) methacrylate, as measured by the transmission of the sample.

In order to assess the ability of nanoparticles based on the brush polymers to undergo a phase transition and exhibit a lower critical solution temperature, the POLAMA block was chain extended using a combination of diethyleneglycol methacrylate and oligo(ethylene glycol) methacrylate.[27] Nanoparticles prepared from POLAMA4-POEGMA having a composition of 90:10 of diethylene glycol methacrylate and oligo(ethylene glycol methacrylate) respectively, within the POEGMA block, were assessed for their thermoresponsive properties. A cloud point was observed at the expected temperature of 39° C. (FIG. 13), and the cloud point could be adjusted to any desired value between ~20° C. to >90° C. by altering the ratio of the two OEGMA monomers.

Figure 4:
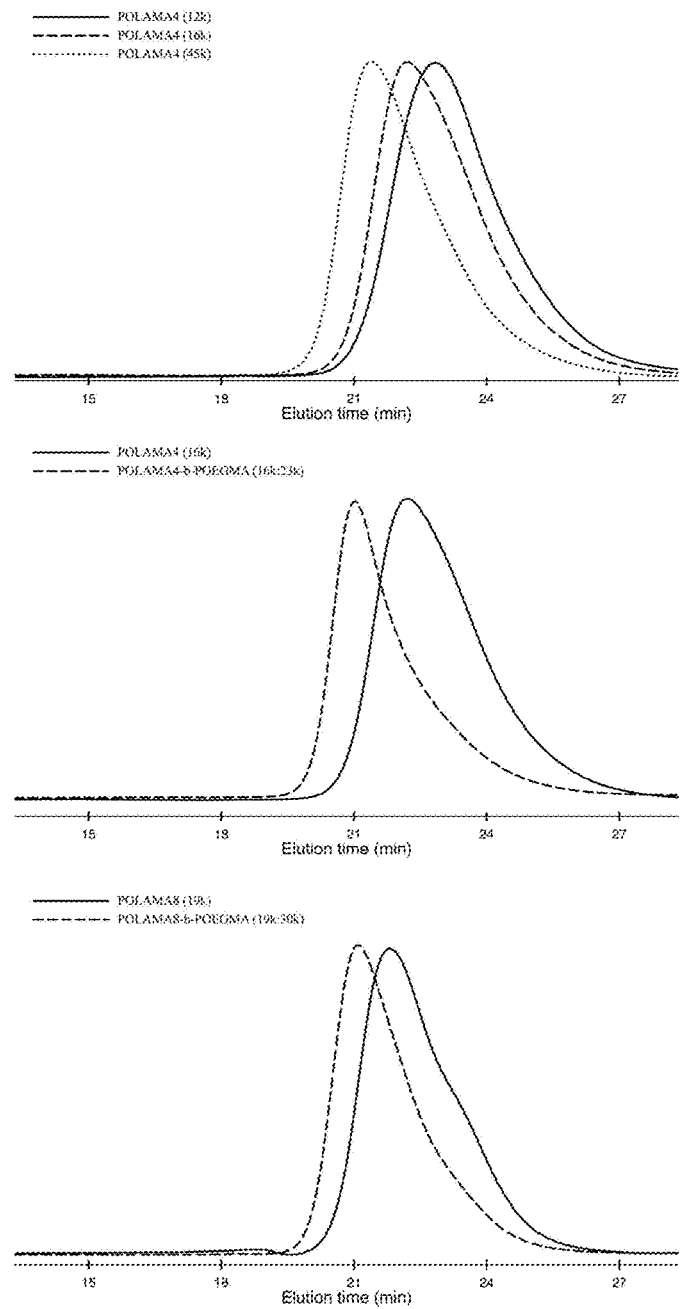
FIG. 4 shows the gel permeation chromatograms of hydrophobic blocks of the disclosure (POLAMA4: 12 kDa, 17 kDa, 45 kDa), showing the capability for controlling the backbone molecular weight by ATRP (top), and the effective chain extension to form a block copolymer of the disclosure (POLAMA4-b-POEGMA) (middle) and (POLAMA8-b-POEGMA) (bottom) dual brush block copolymers.
Figure 5:
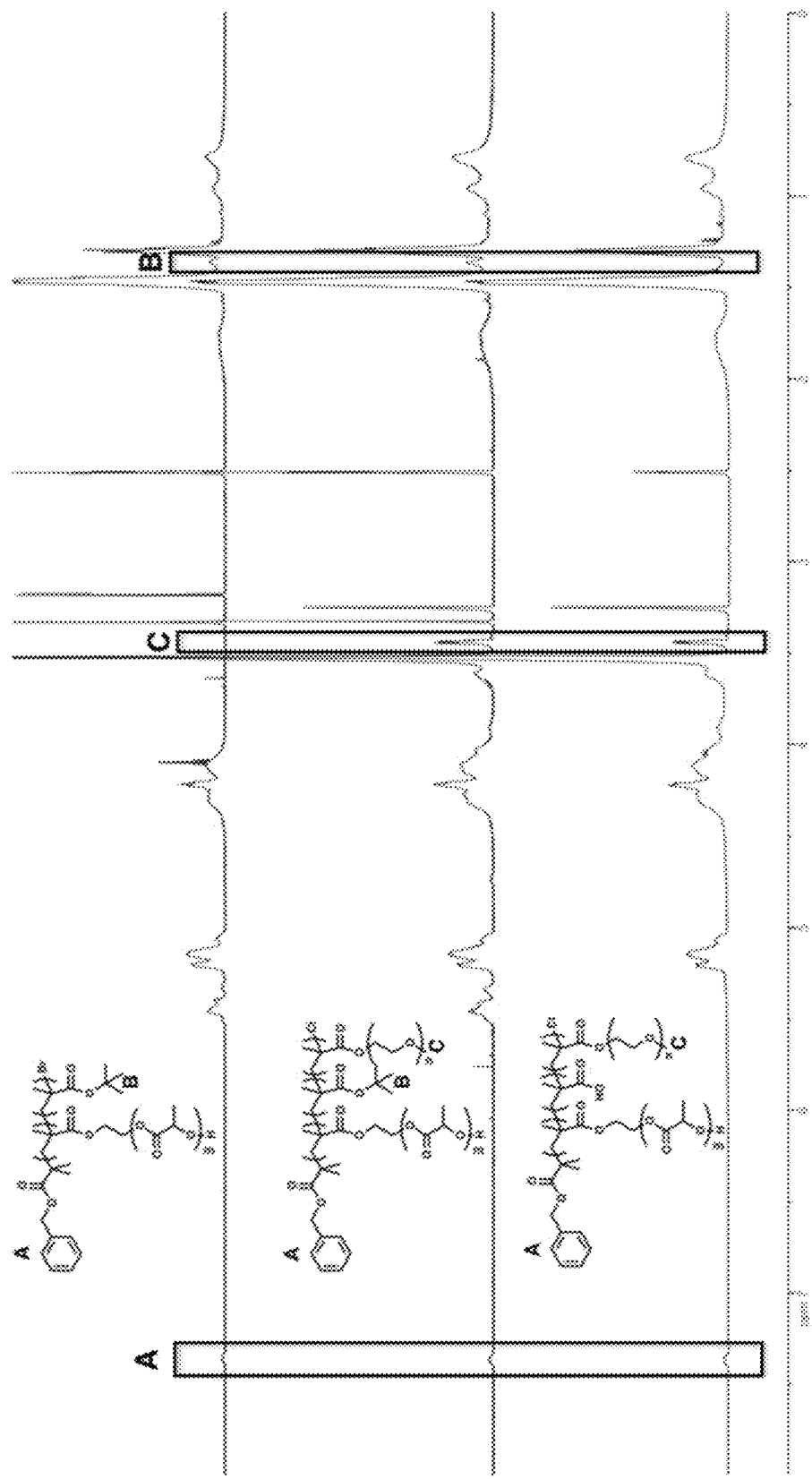
FIG. 5 shows the ¹H-NMR spectrum in DMSO-d6 of hydrophobic blocks: POLAMA4 with 5% tert-butyl methacrylate (top), POLAMA4-b-POEGMA with 5% tert-butyl methacrylate in POLAMA block (middle) and POLAMA4-b-POEGMA with 5% carboxylic acid groups in POLAMA block.

Additionally, the pendant alcohol group on the OLAMA monomer serves as a potential site for facile modification. In order to tune the hydrophobicity of the POLAMA block, the pendant alcohol was acetylated (FIGS. 1 and 2) and the monomer was polymerized using ATRP, as described above (FIG. 4). The resulting polymer exhibited reduced solubility in polar organic solvents such as methanol (compared to the POLAMA polymer without the acetyl groups). Such modifications are useful for potentially tuning the hydrophobic/hydrophilic character of the core domain within the nanoparticles.

Example 2: Nanoparticle Fabrication

Figure 6:
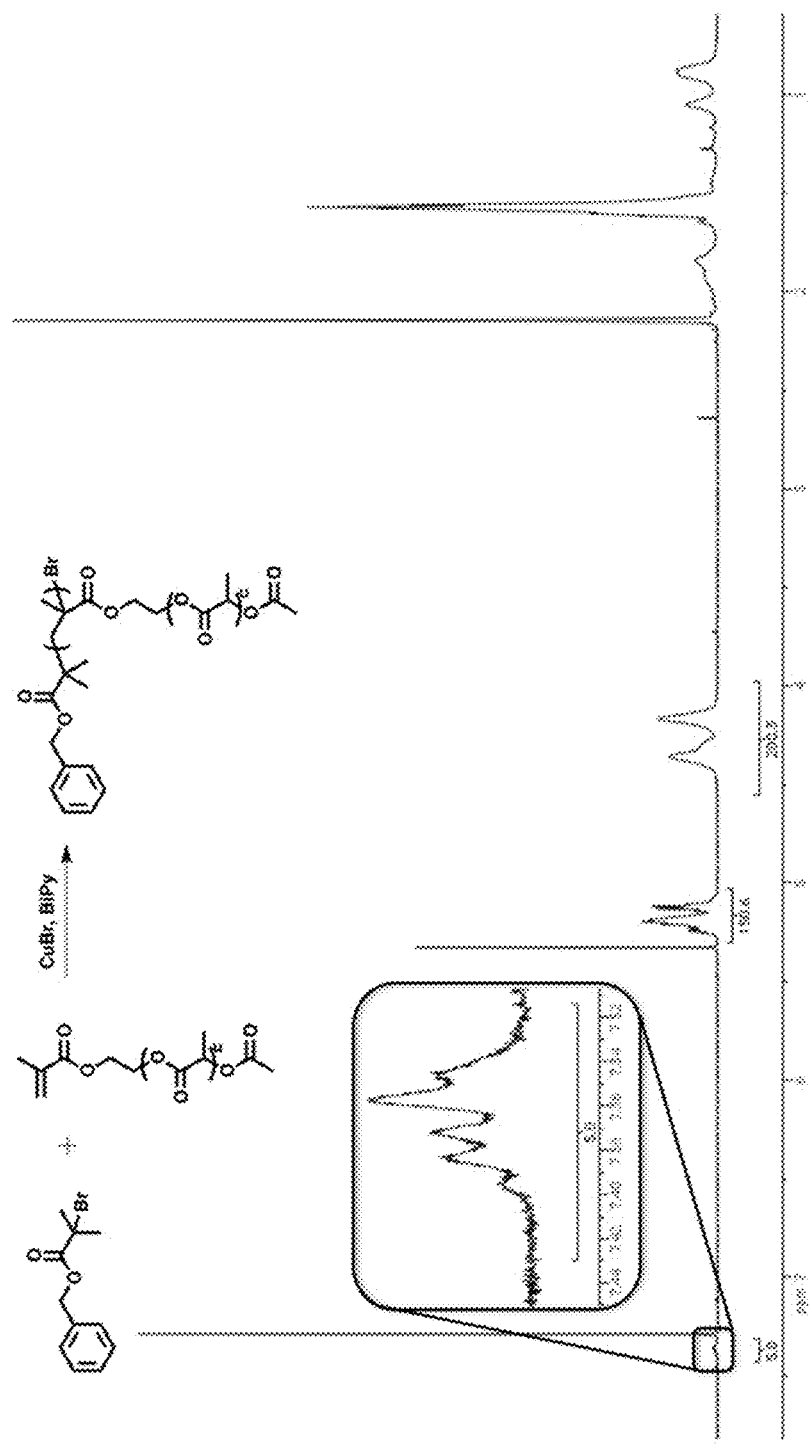
FIG. 6 shows the ¹H-NMR spectrum in CDCl₃ of hydrophobic block (POLAMA4) that is functionalized (acetylated) at the repeat units.
Figure 7:
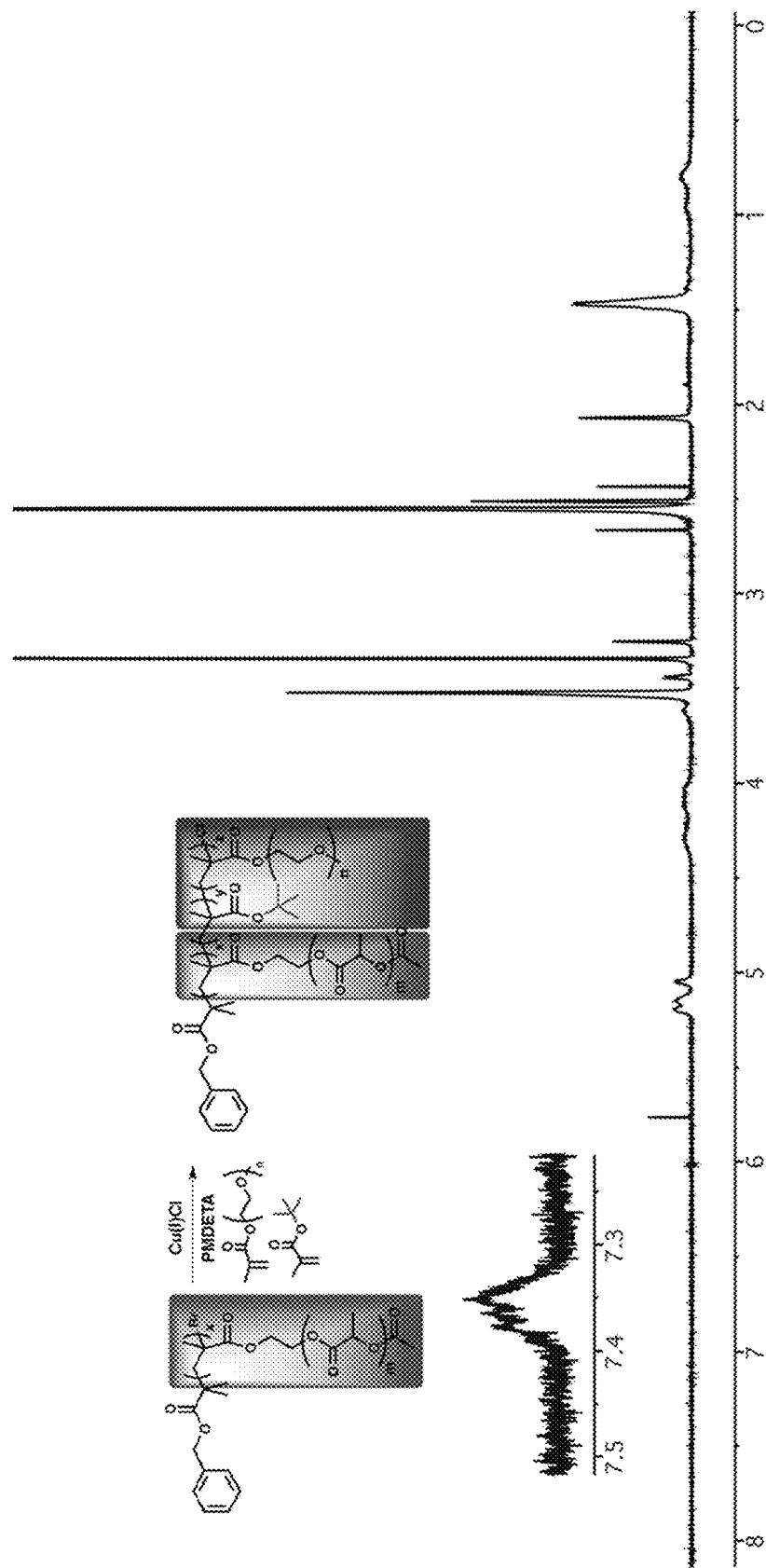
FIG. 7 shows the ¹H-NMR spectrum in DMSO-d6 of the functionalized (acetylated) block copolymer (POLAMA4 (Ac)-b-(P(OEGMA-co-tBMA)), with a specific (4:1) ratio of OEGMA/tBMA.
Figure 8:
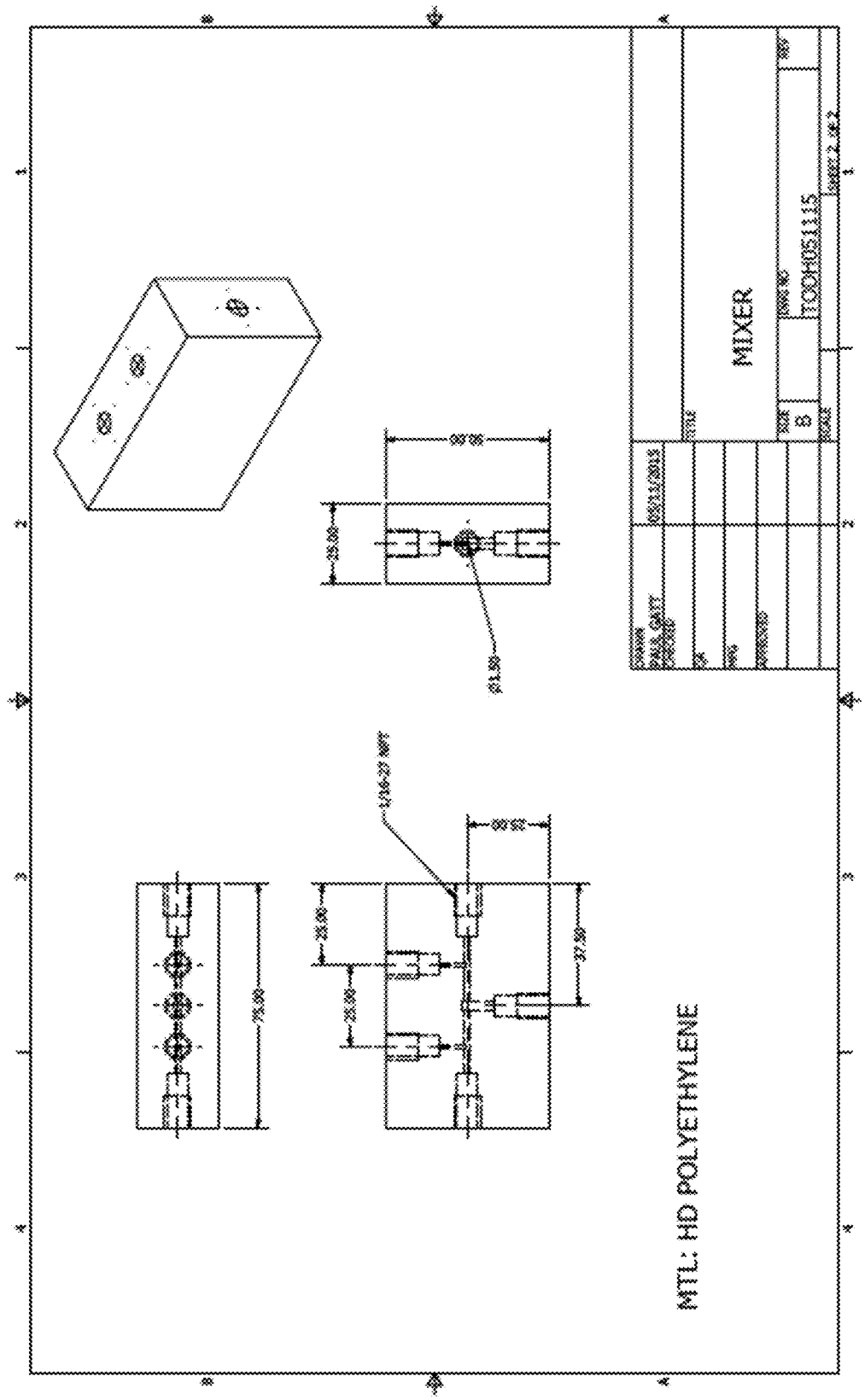
FIG. 8 shows the schematic of the flash nanoprecipitation device utilized to fabricate nanoparticles (NPs) using the block copolymers of the disclosure.

Nanoparticles were fabricated from flash nanoprecipitation using a CIJ-D[26], machined in-house from a polyethylene block (FIG. 6). A syringe containing 3 mL of a 10 mg/mL solution of POLAMA-b-POEGMA polymer in THF (or other organic solvents, see Table 3) was placed in one of the inlets of the CIJ-D. In the case of drug loaded NPs, a syringe containing 3 mL of a 10 mg/mL solution of POLAMA-b-POEGMA polymer and 1 mg/mL of drug in organic solvent was employed. Another syringe containing 3 mL of 10 mM PBS was placed in the remaining available inlet of the CIJ-D. The two syringes were pushed simultaneously and rapidly (1-2 seconds). The solution exited the CIJ-D into a stirring 54 mL solution of 10 mM PBS, resulting in the final solution containing 5% THF and a nanoparticle concentration of 0.5 mg/mL. The solution was left stirring open to the air in a fume hood to evaporate the organic solvent. To change the Reynolds number (and thus the particle size), the flow rate of the impinging action was controlled using a syringe pump (KD Scientific Legato™ 270). The Reynolds number was calculated using:

$$\text{Re} = \sum_{i=1}^{n} \text{Re}_i = \frac{d}{A}\sum_{i=1}^{n}\frac{\rho_i Q_i}{\mu_i} = \frac{4}{\pi d}\sum_{i=1}^{n}\frac{\rho_i Q_i}{\mu_i}$$

where n is the number of streams, d is the inlet diameter (m), A is the cross-sectional area of the pipe (m$^2$), ρ is the fluid density (kg/m$^3$), Q is the volumetric flow rate (m$^3$/s), and μ is the fluid viscosity (kg/m 5).[26]

Figure 9:
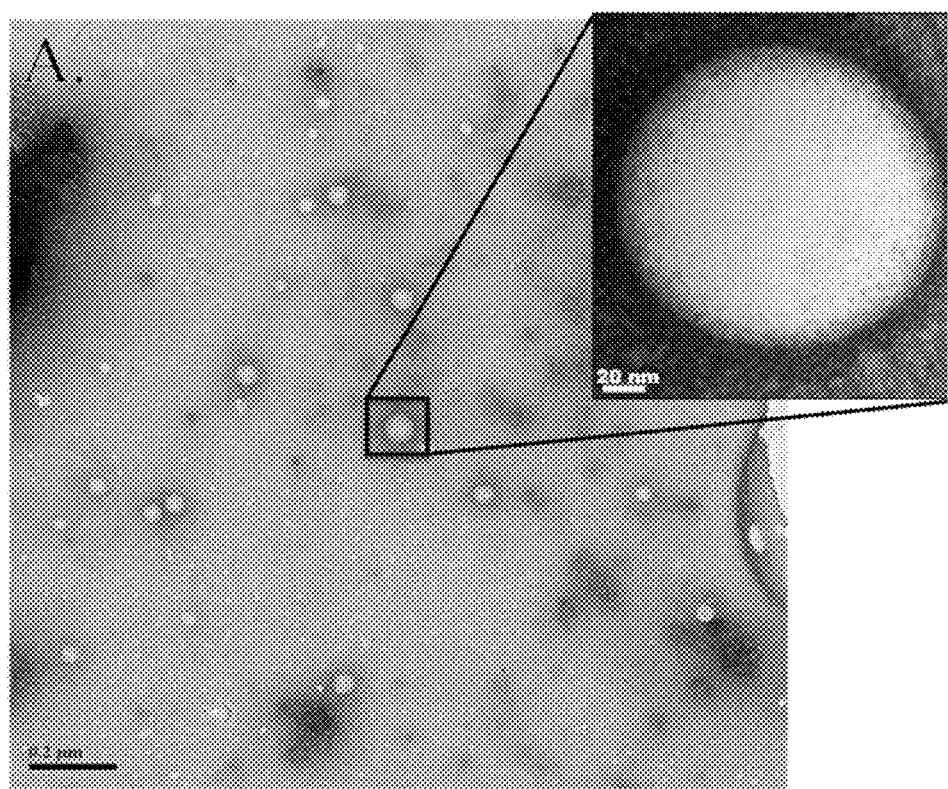
FIG. 9 shows representative TEM images of block copolymers assembled into NPs. Images were obtained after samples were dried and then stained with uranyl acetate.

For nanoparticle preparation, a 10 mg/mL solution of a POLAMA-POEGMA block copolymer (dissolved in THF) was impinged with an equivalent volume of 10 mM phosphate buffered saline (PBS) by simply pushing down on both syringes in a simultaneous manner. The resulting solution was further diluted into PBS to give a final NPs concentration of 0.5 mg/mL. As shown in Table 3, most block copolymers enabled formation of NPs in the 110-160 nm range, a size that is ideal for targeting tumors via the enhanced permeation and retention (EPR) effect for cancer treatment[23] as well as facilitating high circulation times for other therapeutic targets[24]. The NPs also exhibited a polydispersity typically equal to or below 0.1, indicating a relatively narrow NP size distribution[25]; this is particularly true relative to the alternative emulsion-based method used for NP assembly, which typically yields polydispersities >0.2 for PEG-PLA NP.[25] Transmission electron microscopy (TEM) images confirm both the size and the relatively narrow size distribution of the NPs produced. (FIG. 9).

Figure 10:
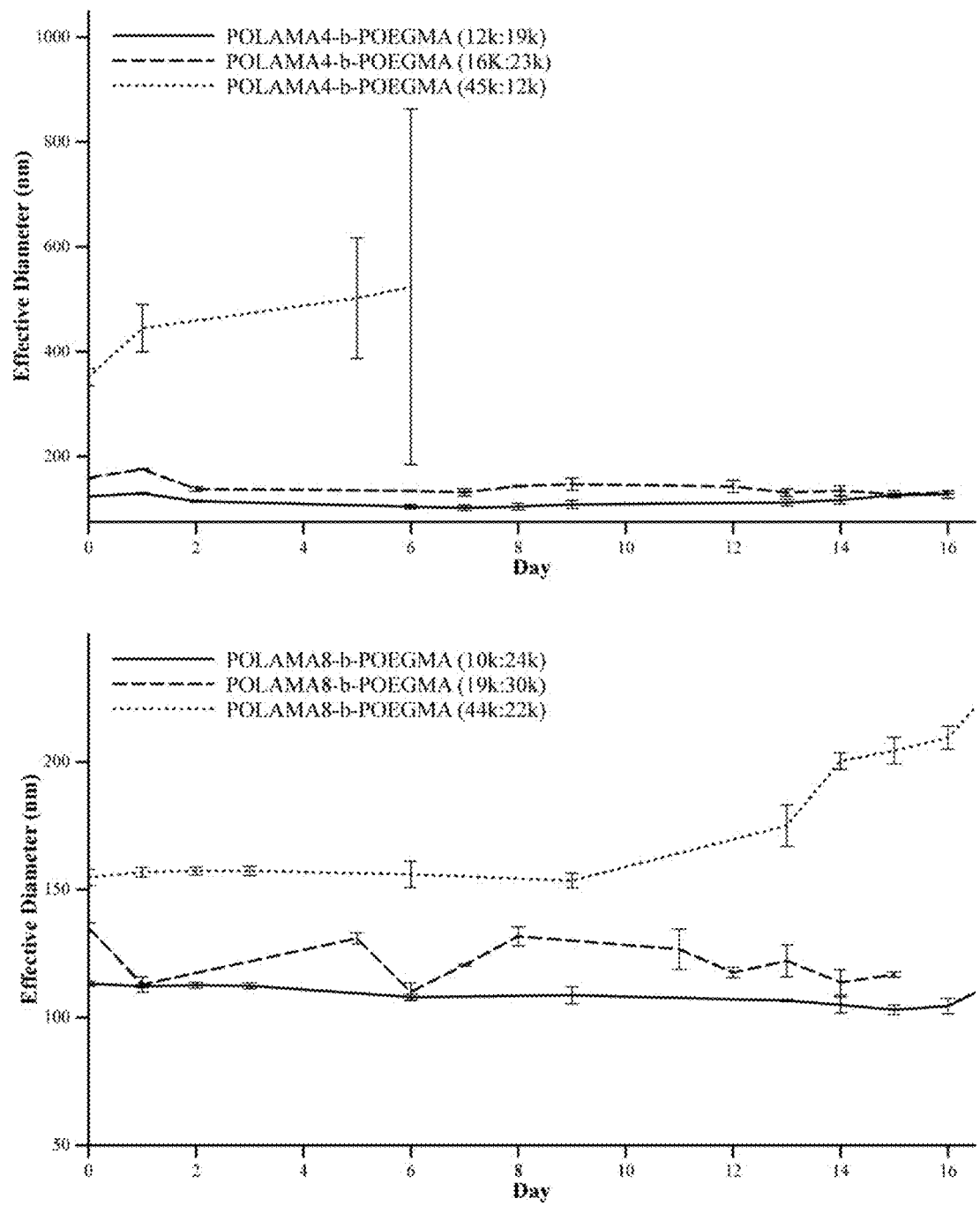
FIG. 10 shows the effective diameter of NPs over time while incubated at 37° C. in 10 mM PBS.

The size of the nanoparticles produced was assessed as a function of time via dynamic light scattering to confirm both the stability of the self-assembled structures as well as the colloidal stability of the NPs themselves (FIG. 10). Most NPs produced remained stable in excess of two weeks in PBS at 37° C., indicating their potential for long-term circulation and effective storage.

Figure 11:
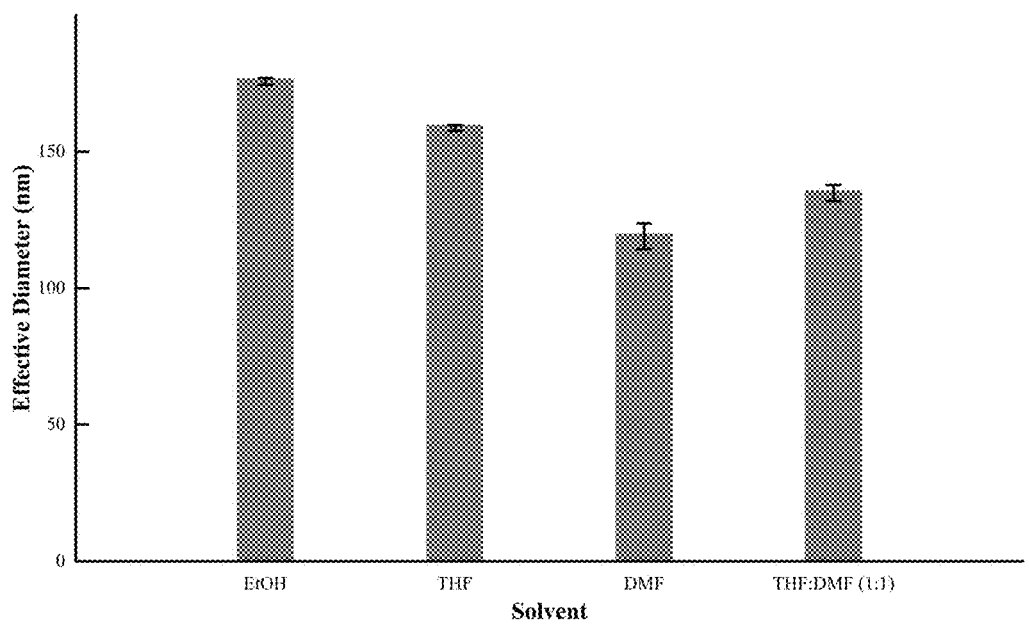
FIG. 11 shows the effect of organic solvent on the diameter of NPs formed via flash nanoprecipitation.
Figure 12:
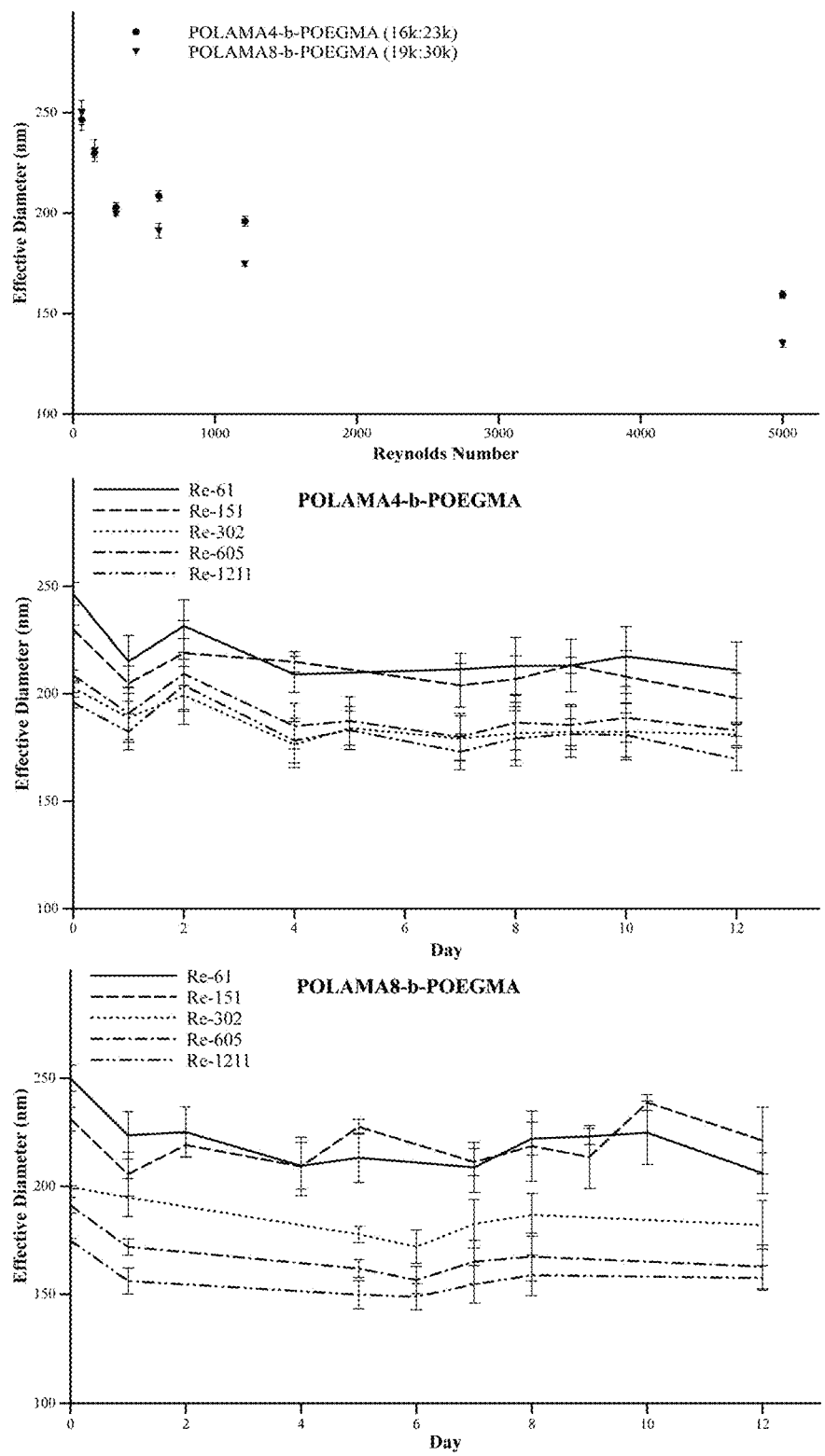
FIG. 12 shows the effect of Reynolds number on NP size and resulting stability in 10 mM PBS at 37° C.

To determine the effect of organic solvent selection during the impinging process on the size of the resulting NPs, the use of ethanol and DMF as well as a mixture of DMF/THF were investigated (FIG. 11). A more polar solvent (compared to THF) is desirable for drug loading of hydrophilic drugs such as the hydrochloride salt of doxorubicin (DOX-HCl), which is insoluble in THF. Interestingly, the choice of solvent also dictated NP size, with DMF (the most polar solvent) giving rise to the smallest NPs and ethanol resulting in NPs with a larger diameter. Previous studies have shown a correlation of an increased solvent miscibility with water leading to smaller NPs.[9a,26] In our observations, ethanol was the outlier, potentially due to the comparatively lower solubility of the copolymer in the solvent. Alternately, nanoparticle size can be tuned by varying the flow rates (and thus the Reynolds number) of the block copolymer solution (in THF) and PBS during the impingement process (FIG. 12). Lower Re numbers (i.e. lower flow rates during impingement) result in larger NPs, with NPs of size 135 to 250 nm in diameter achievable with (by example) POLAMA8-POEGMA (19K:48K) by simply changing the flow rate; note that NPs over the whole size range produced all remained stable in 10 mM PBS over at least two weeks (FIG. 12).

Example 3: In Vitro Cytotoxicity

Figure 14:
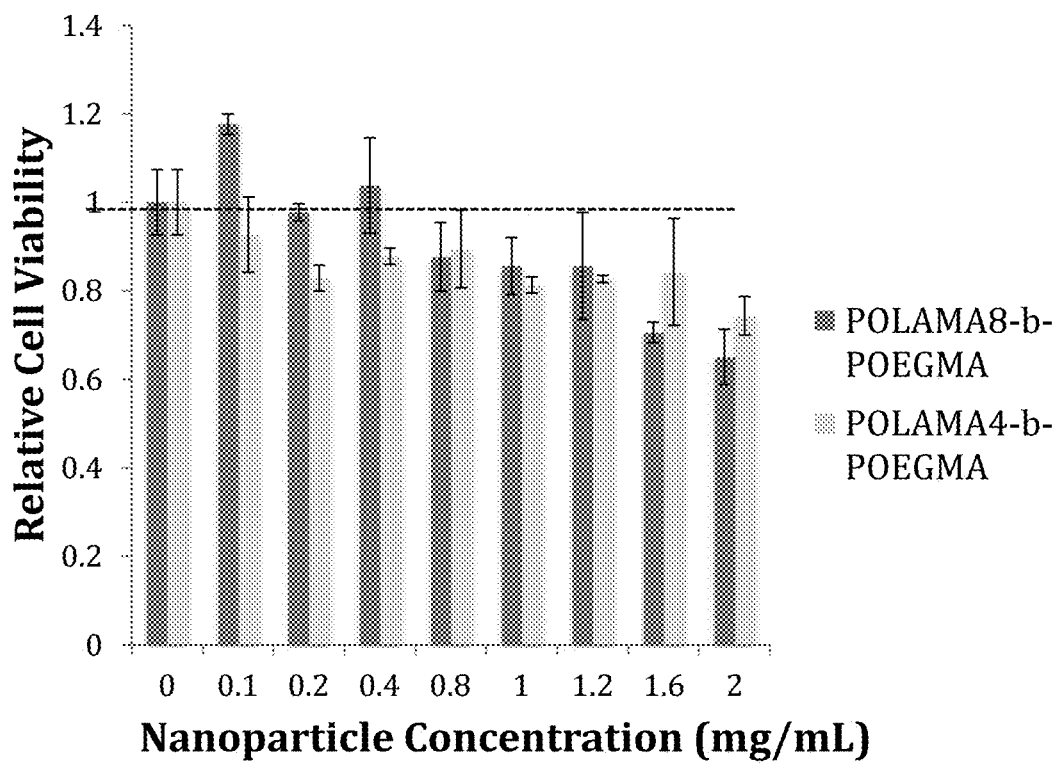
FIG. 14 shows in vitro cell cytotoxicity assay data as measured via a resazurin assay on block copolymers of the disclosure (POLAMA4-b-POEGMA) and (POLAMA8-b-POEGMA) NPs.
Figure 15:
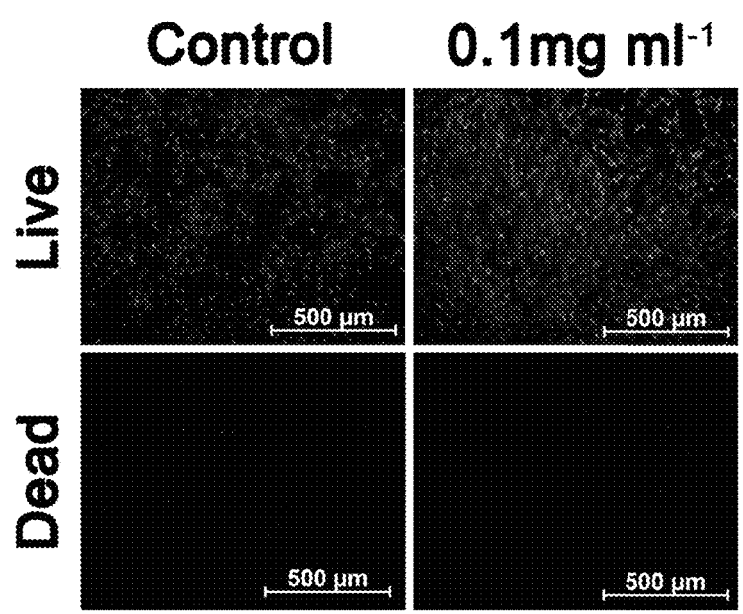
FIG. 15 shows in vitro cell cytotoxicity assay data as measured via a LIVE/DEAD assay with NP concentrations at 0.1 mg/mL.

The cytocompatability of the nanoparticles was assessed via a resazurin cell viability assay[28]. The polymer samples were sterilized via filtration through a non-pyrogenic Acrodisc® syringe filter (0.45 μm Supor® membrane). NIH 3T3 mouse fibroblasts were plated in a 96-well plate at a density of 10,000 cells/well, along with 150 μL of DMEM with 10% FBS and 1% penicillin/streptomycin. The cells were allowed to proliferate in an incubator (37° C., 5% $CO_2$) for 24 hrs, after which cells in experimental wells were treated with POLAMA-b-POEGMA polymers (Table 2, entries 3 and 8) at concentrations ranging from 0.1-2 mg/mL. The cells were incubated for another 24 hrs, after which the resazurin solution was applied to the cells such that the final concentration of resazurin in each well was 10 μg/mL. The cells were then placed in the incubator for 4 hrs, and the fluorescence of converted resorufin was subsequently measured using a Perkin Elmer Victor[3] V microplate reader ($\lambda_{Exc}$=531 nm, $\lambda_{Emi}$=572 nm). The background fluorescence of the particles and the media was accounted for by subtracting the fluorescence reading of blank wells from the corresponding experimental wells. The results of the assay are presented as relative values compared to a cell control. Error bars represent standard deviations of the measured cell viability percentages (n=4). Two representative NP formulations, POLAMA4-b-POEGMA and POLAMA8-b-POEGMA, were tested over a 24 hour exposure time (FIG. 14). Neither NP formulation exhibited significant in vitro cytotoxicity, even at concentrations of 1 mg/mL. Furthermore, no in vitro cytotoxicity was observed when a LIVE/DEAD assay was employed with a polymer nanoparticle concentration of 0.1 mg/mL (FIG. 15). Therefore, NPs based on POLAMA-b-POEGMA brush polymers are cytocompatible and are thus amenable for potential in vivo use.

Example 4: Drug Loading

The same flash nanoprecipitation procedure outlined above was used for drug encapsulation. In a solution of 10 mg/mL of polymer, 10 w/w % of drug vs. polymer was added; THF was used for paclitaxel (PTX) and DMF was used for doxorubicin hydrochloride (DOX-HCl) and doxorubicin free base (DOX). Following, ultrafiltration of drug loaded nanoparticles was performed using Pall Corporation Microsep™ Advance centrifugal device (MWCO: 10 kDa) and centrifuged at 3000×g for 20 minutes at 15° C. using a Beckman Coulter Allegra™ X-12R centrifuge. Paclitaxel (PTX) concentration was measured using a Agilent liquid chromatography coupled with mass spectrometry (LCMS) system comprised of an Agilent 1200 system equipped with an autosampler, pump, and UV/visible detector using a Dionex Acclaim 120 C18 column (250×4.6 mm, 5 μm; pore size: 120 Å) at 40° C.; 40% acetonitrile was used during equilibration with an increasing gradient to 100% acetonitrile used for elution. PTX concentration was analyzed using an Agilent 6340 Ion Trap mass spectrometer and calculated using the $(M+H)^+$ peak. A calibration curve covering the concentration range 0.8-50 μg/mL ($R^2$=0.99) was established. Doxorubicin concentration was measured using a Perkin Elmer Victor[3] V microplate reader, using a calibration curve ranging from 3.3 μg/mL to 0.532 mg/mL ($R^2$=0.99) for quantification of drug concentration. 100 μL of the supernatant solution of DOX-HCl and 100 μL of 5% DMF in 10 mM PBS (to be used for background correction) was loaded onto a 96-well plate in triplicates and the absorbance was measured ($\lambda_{abs}$=450 nm).

Dynamic light scattering (DLS) analysis of NPs before and after ultracentrifugation revealed no change in size during the purification process, confirming that centrifugation does not induce dis-assembly of the NPs. The resulting NPs were but significantly larger than blank NPs fabricated using the same recipes (Table 4), a result that is expected when utilizing flash nanoprecipitation.[29] However, drug loading into the NPs was extremely efficient, with HPLC analysis indicating >96% encapsulation efficiency of PTX within the NPs. Drug loading of NPs with DOX-HCl using the same methodology and DMF as the organic solvent during the impinging process resulted in a lower but still significant 41% encapsulation efficacy; this lower drug loading efficacy with DOX-HCl is consistent with the significantly higher hydrophilicity of DOX-HCl. Conversion of the drug into the free base (i.e. more hydrophobic) form enabled higher drug loadings of ~60%, similar to those achieved with conventional PL(G)A-PEG nanoparticles.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term

TABLE 1

Experimental Conditions for the Preparation of the POLAMA Block

| Monomer | Entry | M/I | Target $M_n$ (kDA) | $M_n$ (NMR) (kDa) | Conversion (NMR) | GPC | | |
| --- | --- | --- | --- | --- | --- | --- | --- | --- |
| | | | | | | $M_n$ (kDa) | $M_w$ (kDa) | Đ |
| OLAMA4 | 12K | 30 | 12.5 | 11.7 | 0.93 | 15.3 | 19.5 | 1.27 |
| | 16K | 50 | 20.9 | 16.5 | 0.79 | 18.3 | 22.9 | 1.25 |
| | 45K | 150 | 62.8 | 45.0 | 0.72 | 25.2 | 31.5 | 1.25 |

TABLE 1-continued

Experimental Conditions for the Preparation of the POLAMA Block

| Monomer | Entry | M/I | Target $M_n$ (kDA) | $M_n$ (NMR) (kDa) | Conversion (NMR) | GPC $M_n$ (kDa) | GPC $M_w$ (kDa) | D |
|---|---|---|---|---|---|---|---|---|
| OLAMA8 | 10K | 21 | 14.8 | 10.0 | 0.68 | 16.7 | 20.5 | 1.23 |
|  | 19K | 42 | 29.7 | 18.8 | 0.63 | 22.3 | 27.1 | 1.22 |
|  | 44K | 105 | 74.1 | 43.8 | 0.59 | 25.5 | 32.2 | 1.26 |

*All polymerizations were conducted in DMSO at 70° C. using CuBr and BiPy at a molar ratio of 1:2.5.
M/I = monomer:initiator ratio.

TABLE 2

Experimental Conditions and Properties of Block Copolymers

| Entry | MI | M/MI | Target $M_n$ (kDa) | $M_n$ (NMR) (kDa) | Conversion (NMR) | Monomer Ratio (OLAMA:OEGMA) | D |
|---|---|---|---|---|---|---|---|
| 1 | POLAMA 4 (12K) | 50 | 37.5 | 31.1 | 0.83 | 41:59 | 1.30 |
| 2 | POLAMA 4 (16K) | 25 | 33.4 | 24.6 | 0.74 | 67:23 | 1.28 |
| 3 | POLAMA 4 (16K) | 50 | 45.9 | 38.6 | 0.84 | 48:52 | 1.28 |
| 4 | POLAMA 4 (16K) | 125 | 83.4 | 42.8 | 0.51 | 38:62 | 1.28 |
| 5 | POLAMA 4 (45K) | 50 | 87.8 | 56.7 | 0.65 | 77:23 | 1.29 |
| 6 | POLAMA 8 (10K) | 50 | 39.8 | 33.8 | 0.85 | 25:75 | 1.36 |
| 7 | POLAMA 8 (19K) | 25 | 42.2 | 37.2 | 0.88 | 55:45 | 1.19 |
| 8 | POLAMA 8 (19K) | 50 | 54.7 | 48.9 | 0.89 | 38:62 | 1.22 |
| 9 | POLAMA 8 (19K) | 125 | 92.2 | 67.5 | 0.73 | 23:77 | 1.33 |
| 10 | POLAMA 8 (44K) | 50 | 99.1 | 66.0 | 0.67 | 65:35 | 1.33 |

*All polymerizations were conducted using CuCl and BiPy at a molar ratio of 1:2.5.
M/I = monomer:initiator ratio.

TABLE 3

Size and polydispersity of NPs made using THF as the organic solvent, as determined by DLS.

| Entry (from Table 2) | NP Diameter (nm) | Polydispersity |
|---|---|---|
| 1 | 123 ± 1 | 0.10 |
| 2 | 245 ± 1 | 0.10 |
| 3 | 159 ± 2 | 0.05 |
| 4 | 139 ± 1 | 0.06 |
| 5 | 351 ± 16 | 0.12 |
| 6 | 113 ± 1 | 0.06 |
| 7 | 112 ± 1 | 0.02 |
| 8 | 135 ± 2 | 0.12 |
| 9 | 140 ± 2 | 0.08 |
| 10 | 155 ± 3 | 0.07 |

TABLE 4

Drug loading efficiency within NPs at 10% w/w.

| Drug | Organic Solvent | NP Diameter (nm) | Polydispersity | Drug Loading Efficacy |
|---|---|---|---|---|
| PTX | THF | 170 ± 3 | 0.14 | >96% |
| DOX-HCl | DMF | 145 ± 9 | 0.25 | 41% |
| DOX | DMF | 264 ± 21 | 0.36 | 61% |

REFERENCES 1. (a) Jain, R. A., The manufacturing techniques of various drug loaded biodegradable poly(lactide-co-glycolide) (PLGA) devices. *Biomaterials* 2000, 21 (23), 2475-2490; (b) Danhier, F.; Ansorena, E.; Silva, J. M.; Coco, R.; Le Breton, A.; Preat, V., PLGA-based nanoparticles: An overview of biomedical applications. *Journal of Controlled Release* 2012, 161 (2), 505-522; (c) Zizelmann, C.; Schoen, R.; Metzger, M. C.; Schmelzeisen, R.; Schramm, A.; Dott, B.; Bormann, K. H.; Gellrich, N. C., Bone formation after sinus augmentation with engineered bone. *Clin Oral Implan Res* 2007, 18 (1), 69-73.
2. Azimi, B.; Nourpanah, P.; Rabiee, M.; Arbab, S., Poly (lactide-co-glycolide) Fiber: An Overview. *J Eng Fiber Fabr* 2014, 9 (1), 47-66.

3. Hickey, T.; Kreutzer, D.; Burgess, D. J.; Moussy, F., Dexamethasone/PLGA microspheres for continuous delivery of an anti-inflammatory drug for implantable medical devices. *Biomaterials* 2002, 23 (7), 1649-56.

4. (a) Tamai, H.; Igaki, K.; Kyo, E.; Kosuga, K.; Kawashima, A.; Matsui, S.; Komori, H.; Tsuji, T.; Motohara, S.; Uehata, H., Initial and 6-month results of biodegradable poly-l-lactic acid coronary stents in humans. *Circulation* 2000, 102 (4), 399-404; (b) Wang, X. T.; Venkatraman, S. S.; Boey, F. Y. C.; Loo, J. S. C.; Tan, L. P., Controlled release of sirolimus from a multilayered PLGA stent matrix. *Biomaterials* 2006, 27 (32), 5588-5595.

5. Smeets, N. M. B.; Patenaude, M.; Kinio, D.; Yavitt, F. M.; Bakaic, E.; Yang, F. C.; Rheinstadter, M.; Hoare, T., Injectable hydrogels with in situ-forming hydrophobic domains: oligo(D,L-lactide) modified poly(oligoethylene glycol methacrylate) hydrogels. *Polymer Chemistry* 2014, 5 (23), 6811-6823.

6. Makadia, H. K.; Siegel, S. J., Poly Lactic-co-Glycolic Acid (PLGA) as Biodegradable Controlled Drug Delivery Carrier. *Polymers (Basel)* 2011, 3 (3), 1377-1397.

7. Xiao, R. Z.; Zeng, Z. W.; Zhou, G. L.; Wang, J. J.; Li, F. Z.; Wang, A. M., Recent advances in PEG-PLA block copolymer nanoparticles. *International Journal of Nanomedicine* 2010, 5, 1057-1065.

8. (a) Gref, R.; Luck, M.; Quellec, P.; Marchand, M.; Dellacherie, E.; Harnisch, S.; Blunk, T.; Muller, R. H., 'Stealth' corona-core nanoparticles surface modified by polyethylene glycol (PEG): influences of the corona (PEG chain length and surface density) and of the core composition on phagocytic uptake and plasma protein adsorption. *Colloid Surface B* 2000, 18 (3-4), 301-313; (b) Knop, K.; Hoogenboom, R.; Fischer, D.; Schubert, U. S., Poly(ethylene glycol) in drug delivery: pros and cons as well as potential alternatives. *Angew Chem Int Ed Engl* 2010, 49 (36), 6288-308; (c) Vonarbourg, A.; Passirani, C.; Saulnier, P.; Benoit, J. P., Parameters influencing the stealthiness of colloidal drug delivery systems. *Biomaterials* 2006, 27 (24), 4356-73; (d) Dai, Q.; Walkey, C.; Chan, W. C., Polyethylene glycol backfilling mitigates the negative impact of the protein corona on nanoparticle cell targeting. *Angew Chem Int Ed Engl* 2014, 53 (20), 5093-6; (e) Gillies, E. R.; Dy, E.; Frechet, J. M.; Szoka, F. C., Biological evaluation of polyester dendrimer: poly(ethylene oxide) "bow-tie" hybrids with tunable molecular weight and architecture. *Mol Pharm* 2005, 2 (2), 129-38.

9. (a) Cheng, J.; Teply, B. A.; Sherifi, I.; Sung, J.; Luther, G.; Gu, F. X.; Levy-Nissenbaum, E.; Radovic-Moreno, A. F.; Langer, R.; Farokhzad, O. C., Formulation of functionalized PLGA-PEG nanoparticles for in vivo targeted drug delivery. *Biomaterials* 2007, 28 (5), 869-876; (b) Piazza, J.; Hoare, T.; Molinaro, L.; Terpstra, K.; Bhandari, J.; Selvaganapathy, P. R.; Gupta, B.; Mishra, R. K., Haloperidol-loaded intranasally administered lectin functionalized poly(ethylene glycol)-block-poly(D,L)-lactic-co-glycolic acid (PEG-PLGA) nanoparticles for the treatment of schizophrenia. *Eur J Pharm Biopharm* 2014, 87 (1), 30-9.

10. (a) Wang, S.; Dormidontova, E. E., Nanoparticle design optimization for enhanced targeting: Monte Carlo simulations. *Biomacromolecules* 2010, 11 (7), 1785-95; (b) Martinez-Veracoechea, F. J.; Frenkel, D., Designing super selectivity in multivalent nano-particle binding. *Proc Natl Acad Sci USA* 2011, 108 (27), 10963-8.

11. (a) Joralemon, M. J.; O'Reilly, R. K.; Hawker, C. J.; Wooley, K. L., Shell click-crosslinked (SCC) nanoparticles: a new methodology for synthesis and orthogonal functionalization. *J Am Chem Soc* 2005, 127 (48), 16892-9; (b) O'Reilly, R. K.; Hawker, C. J.; Wooley, K. L., Cross-linked block copolymer micelles: functional nanostructures of great potential and versatility. *Chem Soc Rev* 2006, 35 (11), 1068-83.

12. Oh, J. K., Polylactide (PLA)-based amphiphilic block copolymers: synthesis, self-assembly, and biomedical applications. *Soft Matter* 2011, 7 (11), 5096-5108.

13. Rowe, M. A.; Hammer, B. A. G.; Boyes, S. G., Synthesis of surface-initiated stimuli-responsive diblock copolymer brushes utilizing a combination of ATRP and RAFT polymerization techniques. *Macromolecules* 2008, 41 (12), 4147-4157.

14. Lego, B.; Francois, M.; Skene, W. G.; Giasson, S., Polymer Brush Covalently Attached to OH-Functionalized Mica Surface via Surface-Initiated ATRP: Control of Grafting Density and Polymer Chain Length. *Langmuir* 2009, 25 (9), 5313-5321.

15. (a) Akimoto, J.; Nakayama, M.; Sakai, K.; Okano, T., Temperature-Induced Intracellular Uptake of Thermoresponsive Polymeric Micelles. *Biomacromolecules* 2009, 10 (6), 1331-1336; (b) Cao, Z. Q.; Yu, Q. M.; Xue, H.; Cheng, G.; Jiang, S. Y., Nanoparticles for Drug Delivery Prepared from Amphiphilic PLGA Zwitterionic Block Copolymers with Sharp Contrast in Polarity between Two Blocks. *Angew Chem Int Edit* 2010, 49 (22), 3771-3776; (c) Nam, K. W.; Watanabe, J.; Ishihara, K., Characterization of the spontaneously forming hydrogels composed of water-soluble phospholipid polymers. *Biomacromolecules* 2002, 3 (1), 100-105; (d) Watanabe, J.; Eriguchi, T.; Ishihara, K., Cell adhesion and morphology in porous scaffold based on enantiomeric poly(lactic acid) graft-type phospholipid polymers. *Biomacromolecules* 2002, 3 (6), 1375-1383.

16. Saeed, A. O.; Dey, S.; Howdle, S. M.; Thurecht, K. J.; Alexander, C., One-pot controlled synthesis of biodegradable and biocompatible co-polymer micelles. *J Mater Chem* 2009, 19 (26), 4529-4535.

17. Ishimoto, K.; Arimoto, M.; Okuda, T.; Yamaguchi, S.; Aso, Y.; Ohara, H.; Kobayashi, S.; Ishii, M.; Morita, K.; Yamashita, H.; Yabuuchi, N., Biobased Polymers: Synthesis of Graft Copolymers and Comb Polymers Using Lactic Acid Macromonomer and Properties of the Product Polymers. *Biomacromolecules* 2012, 13 (11), 3757-3768.

18. Zhang, K. R.; Tang, X.; Zhang, J.; Lu, W.; Lin, X.; Zhang, Y.; Tian, B.; Yang, H.; He, H. B., PEG-PLGA copolymers: Their structure and structure-influenced drug delivery applications. *J Control Release* 2014, 183, 77-86.

19. Shipp, D. A.; Wang, J. L.; Matyjaszewski, K., Synthesis of acrylate and methacrylate block copolymers using atom transfer radical polymerization. *Macromolecules* 1998, 31 (23), 8005-8008.

20. Han, J.; Zhu, Z. X.; Qian, H. T.; Wohl, A. R.; Beaman, C. J.; Hoye, T. R.; Macosko, C. W., A simple confined impingement jets mixer for flash nanoprecipitation. *J Pharm Sci-Us* 2012, 101 (10), 4018-4023.

21. (a) Johnson, B. K.; Prud'homme, R. K., Flash Nano-Precipitation of organic actives and block copolymers using a confined impinging jets mixer. *Aust J Chem* 2003, 56 (10), 1021-1024; (b) Johnson, B. K.; Prud'homme, R. K., Chemical processing and micromixing in confined impinging jets. *Aiche J* 2003, 49 (9), 2264-2282.

22. Kim, Y.; Chung, B. L.; Ma, M. M.; Mulder, W. J. M.; Fayad, Z. A.; Farokhzad, O. C.; Langer, R., Mass Pro- 23. Iyer, A. K.; Khaled, G.; Fang, J.; Maeda, H., Exploiting the enhanced permeability and retention effect for tumor targeting. *Drug Discov Today* 2006, 11 (17-18), 812-818.
24. Yoo, J. W.; Chambers, E.; Mitragotri, S., Factors that Control the Circulation Time of Nanoparticles in Blood: Challenges, Solutions and Future Prospects. *Curr Pharm Design* 2010, 16 (21), 2298-2307.
25. Venkatraman, S. S.; Jie, P.; Min, F.; Freddy, B. Y. C.; Leong-Huat, G., Micelle-like nanoparticles of PLA-PEG-PLA triblock copolymer as chemotherapeutic carrier. *Int J Pharm* 2005, 298 (1), 219-232.
26. Bilati, U.; Allemann, E.; Doelker, E., Development of a nanoprecipitation method intended for the entrapment of hydrophilic drugs into nanoparticles. *Eur J Pharm Sci* 2005, 24 (1), 67-75.
27. Lutz, J. F.; Hoth, A., Preparation of ideal PEG analogues with a tunable thermosensitivity by controlled radical copolymerization of 2-(2-methoxyethoxy)ethyl methacrylate and oligo(ethylene glycol) methacrylate. *Macromolecules* 2006, 39 (2), 893-896.
28. Voytik-Harbin, S. L.; Brightman, A. O.; Waisner, B.; Lamar, C. H.; Badylak, S. F., Application and evaluation of the alamarBlue assay for cell growth and survival of fibroblasts. *In Vitro Cell Dev-An* 1998, 34 (3), 239-246.
29. Pustulka, K. M.; Wohl, A. R.; Lee, H. S.; Michel, A. R.; Han, J.; Hoye, T. R.; McCormick, A. V.; Panyam, J.; Macosko, C. W., Flash Nanoprecipitation: Particle Structure and Stability. *Mol Pharmaceut* 2013, 10 (11), 4367-4377.

The invention claimed is:

1. A brush amphiphilic block copolymer, comprising
a) at least one hydrophilic block comprising between 2 and 1000 monomeric units of:

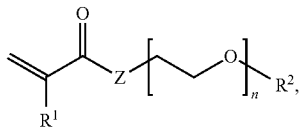

wherein
$R^1$ is H or $(C_1-C_6)$-alkyl, optionally substituted with —COOR or —CON(R)$_2$, wherein R is independently or simultaneously H or $(C_1-C_6)$-alkyl;
$R^2$ is H, $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
 (i) are optionally substituted with halo, OH, or $(C_1-C_6)$-alkyl;
 (ii) 1-3 carbon atoms are optionally replaced with O, NR', or C(=O); and/or
 (iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, a hydrophilic or hydrophobic polymer, heterocycles, or triazoles;
Z is O, NR' or S;
R' is H or $(C_1-C_6)$-alkyl; and
n is 0 or at least 2;

b) at least one hydrophobic block comprising between 2 and 1000 monomeric units of

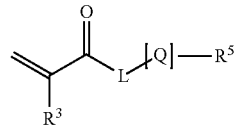

wherein
$R^3$ is H or $(C_1-C_6)$-alkyl, optionally substituted with —COOR or —CON(R)$_2$, wherein R is independently or simultaneously H or $(C_1-C_6)$-alkyl;
L is a linker;
Q is a hydrophobic polymer or copolymer; and
$R^5$ is H, $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
 (i) are optionally substituted with halo, OH, or $(C_1-C_6)$-alkyl;
 (ii) 1-3 carbon atoms are optionally replaced with O, NR', or C(=O); and/or
 (iii) optionally contain one or more functional groups comprising esters, thioesters, amides, ureas, thioureas, carbonates, carbamates, thiocarbamates, ethers, thioethers, primary, secondary, tertiary and/or quaternary amines, sulfone, sulfonate, phosphoesters, phosphoramidates, phosphazenes, a hydrophilic or hydrophobic polymer, heterocycles or triazoles.

2. The brush amphiphilic block copolymer of claim 1, wherein $R^1$ is H or $(C_1-C_3)$-alkyl, optionally substituted with —COOH.

3. The brush amphiphilic block copolymer of claim 1, wherein $R^2$ is H, $(C_1-C_6)$-alkyl, $(C_6)$-aryl, $(C_5-C_6)$-heteroaryl, or $(C_1-C_3)$-alkylene-$(C_6)$-aryl, the latter four groups are
 (i) are optionally substituted with $(C_1-C_3)$-alkyl;
 (ii) 1-3 carbon atoms are optionally replaced with C(=O); and/or
 (iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, a hydrophilic or hydrophobic polymer and/or a heterocycle.

4. The brush amphiphilic block copolymer of claim 1, wherein n is an integer between 2 and 50.

5. The brush amphiphilic block copolymer of claim 1, wherein the monomeric units of the hydrophilic block has the structure

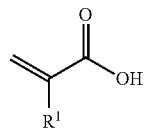

wherein $R^1$ is H or $(C_1-C_6)$-alkyl.

6. The brush amphiphilic block copolymer of claim 1, wherein the hydrophobic polymer or copolymer is a polyurethane, polythiourethane, polyether, polyamide, polyester, polyphosphazine, polyphosphamide, polyphosphodiester, polyureas, polythiourea, polyfumurates, or polyanhydride.

7. The brush amphiphilic block copolymer of claim 1, wherein the linker L is $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups
(i) are optionally substituted with halo, OH, COOH, or $(C_1-C_6)$-alkyl;
(ii) 1-3 carbon atoms are optionally replaced with O, NR', or C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, a hydrophilic or hydrophobic polymer, heterocycle or triazoles.

8. The brush amphiphilic block copolymer of claim 1, wherein the at least one hydrophobic block comprises monomeric units of

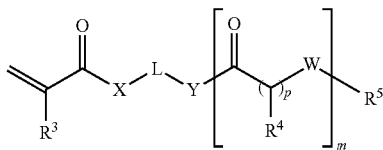

wherein
$R^3$ is H or $(C_1-C_6)$-alkyl, optionally substituted with —COOR or —CON(R)$_2$, wherein R is independently or simultaneously H or $(C_1-C_6)$-alkyl;
each $R^4$ is independently or simultaneously H, OH, COOH, $(C_1-C_{10})$-alkyl, or aryl, wherein the latter two groups may optionally contain functional groups which are esters, acids, thioesters, amides, ureas, thioureas, carbonates, carbamates, thiocarbamates, ethers, thioethers, primary, secondary, tertiary and/or quaternary amines, disulfides, sulfonamides, sulfones, sulfonates, phosphoesters, phosphoramidates, phosphazenes, a hydrophilic or hydrophobic polymer and/or a heterocycle;
$R^5$ is H, $(C_1-C_{20})$-alkyl, $(C_2-C_{24})$-alkenyl, $(C_2-C_{24})$-alkynyl, $(C_6-C_{14})$-aryl, $(C_5-C_{14})$-heteroaryl, or $(C_1-C_{10})$-alkylene-$(C_6-C_{14})$-aryl, wherein the latter 6 groups:
(i) are optionally substituted with halo, OH, or $(C_1-C_6)$-alkyl;
(ii) 1-3 carbon atoms are optionally replaced with O, NR', or C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, a hydrophilic or hydrophobic polymer and/or triazoles;
L is a linker;
X and Y are independently or simultaneously O, NR' or S;
W is O or NR';
R' is H or $(C_1-C_6)$-alkyl;
each p is independently or simultaneously 1, 2, 3, 4, 5, 6, 7, 8, 9 or 10; and
m is at least 2.

9. The brush amphiphilic block copolymer of claim 1, wherein $R^3$ is H or $(C_1-C_3)$-alkyl, optionally substituted with —COOH.

10. The brush amphiphilic block copolymer of claim 1, wherein $R^5$ is H, $(C_1-C_6)$-alkyl, $(C_6)$-aryl, $(C_5-C_6)$-heteroaryl, or $(C_1-C_3)$-alkylene-$(C_6)$-aryl, the latter four groups are
(i) are optionally substituted with $(C_1-C_3)$-alkyl;
(ii) 1-3 carbon atoms are optionally replaced with C(=O); and/or
(iii) optionally contain one or more functional groups comprising esters, thioesters, amides, ureas, thioureas, carbonates, carbamates, thiocarbamates, ethers, thioethers, primary, secondary, tertiary and/or quaternary amines, disulfides, sulfone, sulfonate, phosphoesters, phosphoramidates, phosphazenes, a hydrophilic or hydrophobic polymer and/or a heterocycle.

11. The brush amphiphilic block copolymer of claim 8, wherein each $R^4$ is independently or simultaneously H, $(C_1-C_6)$-alkyl, or $(C_6-C_{14})$-aryl, wherein the latter two groups may optionally contain esters, acids, thioesters, amides, ureas, thioureas, carbonates, carbamates, thiocarbamates, ethers, thioethers, primary, secondary, tertiary and/or quaternary amines, disulfides, sulfonamides, sulfones, sulfonates, phosphoesters, phosphoramidates, phosphazenes and/or a heterocycle.

12. The brush amphiphilic block copolymer of claim 8, wherein p is 1, 2, 3, 4, 5, 6, 7 or 8.

13. The brush amphiphilic block copolymer of claim 1, further comprising one or more additional monomers having the structure

wherein
$R^6$ is H or $(C_1-C_6)$-alkyl, optionally substituted with —COOR, wherein R is H or $(C_1-C_6)$-alkyl; and
K is a functional group which is —R", —OR", —SR", —COOH, —COOR", CON(R")$_2$, —S—S—R", —R"OR", —R"SR", —R"COOR", R"CON(R")$_2$, R"—S—S—R", wherein R" is $(C_1-C_{10})$-alkenyl, $(C_2-C_{10})$-alkynyl, $(C_6-C_{10})$-aryl, $(C_5-C_{10})$-heteroaryl, or $(C_1-C_{10})$-alkylene-$(C_6-C_{10})$-aryl.

14. The brush amphiphilic block copolymer of claim 13, wherein R" is $(C_1-C_6)$-alkyl, $(C_2-C_6)$-alkenyl, $(C_2-C_6)$-alkynyl, $(C_6)$-aryl, $(C_5-C_6)$-heteroaryl, or $(C_1-C_6)$-alkylene-$(C_6)$-aryl.

15. A nanoparticle prepared via the self-assembly or directed assembly of the block copolymers as claimed in claim 1.

16. The nanoparticle of claim 15, wherein the nanoparticle is prepared by flash nanoprecipitation.

17. The nanoparticle of claim 15, further comprising a drug or bioactive agent, wherein the drug or bioactive agent is encapsulated by the nanoparticle.

18. A method for the delivery of a drug or bioactive agent, comprising administering to a patient in need thereof, as nanoparticle as claimed in claim 17.

* * * * *

UNITED STATES PATENT AND TRADEMARK OFFICE
CERTIFICATE OF CORRECTION

PATENT NO. : 10,774,169 B2
APPLICATION NO. : 15/646630
DATED : September 15, 2020
INVENTOR(S) : Lukas Sadowski et al.

Page 1 of 1

It is certified that error appears in the above-identified patent and that said Letters Patent is hereby corrected as shown below:

In the Claims

Claim 13, Column 26, Line 47, "wherein R" is (C1-C10)-alkenyl," should read --wherein R" is (C1-C10)-alkyl, (C2-C10)-alkenyl,--

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*